US006890338B1

(12) United States Patent
Davis et al.

(10) Patent No.: US 6,890,338 B1
(45) Date of Patent: May 10, 2005

(54) METHOD AND APPARATUS FOR PERFORMING ANASTOMOSIS USING RING HAVING TINES WITH WEAK SECTIONS

(75) Inventors: John W. Davis, Mountain View, CA (US); Geoffrey H. Willis, Redwood City, CA (US)

(73) Assignee: Origin Medsystems, Inc., Santa Clara, CA (US)

( * ) Notice: Subject to any disclaimer, the term of this patent is extended or adjusted under 35 U.S.C. 154(b) by 311 days.

(21) Appl. No.: 09/794,670

(22) Filed: Feb. 27, 2001

(51) Int. Cl.[7] .............................................. A61B 17/08
(52) U.S. Cl. ..................... 606/153; 606/213; 606/216
(58) Field of Search ........................... 606/153, 8, 151, 606/152, 213, 215, 216, 219, 221, 155, 157

(56) References Cited

U.S. PATENT DOCUMENTS

| | | | |
|---|---|---|---|
| 3,155,095 A | 11/1964 | Brown | 128/334 |
| 3,166,072 A | 1/1965 | Sullivan, Jr. | 128/334 |
| 3,254,650 A | 6/1966 | Collito | 128/334 |
| 3,258,012 A | 6/1966 | Nakayama et al. | 128/334 |
| 3,606,888 A | 9/1971 | Wilkinson | 128/334 |
| 3,657,744 A | 4/1972 | Ersek | 3/1 |
| 3,683,926 A | 8/1972 | Suzuki | 128/334 R |
| 3,774,615 A | 11/1973 | Lim et al. | 128/334 C |
| 3,908,662 A | 9/1975 | Razgulov et al. | 128/334 R |
| 3,938,528 A | 2/1976 | Bucalo | 128/334 C |
| 3,973,570 A | 8/1976 | Razgulov et al. | 128/337 |
| 3,974,835 A | 8/1976 | Hardy, Jr. | 128/334 C |
| 3,993,078 A | 11/1976 | Bergentz et al. | 123/334 R |
| 4,055,186 A | 10/1977 | Leveen | 128/334 C |
| 4,214,586 A | 7/1980 | Mericle | 128/334 R |

(Continued)

FOREIGN PATENT DOCUMENTS

| | | | | |
|---|---|---|---|---|
| DE | 2822 603 A1 | 11/1979 | | A61F/1/00 |
| DE | 29713335 U1 | 11/1997 | | A61B/17/115 |
| EP | 0 539 237 A1 | 10/1992 | | A61F/2/06 |
| GB | 1181563 | 2/1967 | | A61B/17/11 |
| WO | WO 95/17127 | 6/1995 | | A61B/17/11 |
| WO | WO 95/17128 | 6/1995 | | A61B/17/11 |
| WO | WO 95/35065 | 12/1995 | | A61B/17/068 |
| WO | WO 98/02099 | 1/1998 | | A61B/17/00 |
| WO | WO 98/19630 | 5/1998 | | A61F/2/06 |
| WO | WO 99/21491 | 5/1999 | | A61B/17/115 |
| WO | WO 01/015607 A1 * | 9/2000 | | A61B/17/08 |

OTHER PUBLICATIONS

C.A.F. Tulleken et al., "End–to–End Anastomosis of Small Vessels Using An ND:YAG Laser with a Hemisphertoal Contact Probe," Technical Note, Journal of Neurosurgery, vol. 76, Mar. 1992, pp. 546–549.

Robin H. Heijmen et al., A Novel One–Shot Anastomotic Stapler Prototype for Coronary Bypass Grafting on the Beating Heart: Feasbility in the Pig, The Journal of Thoracic and Cardiovascular Surgery, Jan. 1999, pp. 117–125.

Primary Examiner—Kathryn Odland
(74) Attorney, Agent, or Firm—Law Office of Alan W. Cannon

(57) ABSTRACT

Anastomosis devices, methods and apparatus for installing the devices in the performance of an anastomosis. One example of a device includes a central ring portion from which malleable tines and optionally also fastener elements extend. Each tine may have a weakened section at which it preferentially folds or buckles when subjected to bending force. Each tine can grab and evert tissue around an orifice in which it is installed, as it is moved from an initial to a final configuration. To install a device, the tines are advanced against an anvil to cause them to grab tissue around the orifice and curl radially. The anvil is then retracted to fold the tines so their curled ends move radially outward.

16 Claims, 14 Drawing Sheets

U.S. PATENT DOCUMENTS

| | | | |
|---|---|---|---|
| 4,214,587 A | 7/1980 | Sakura | 128/334 R |
| 4,233,981 A | 11/1980 | Schomacher | 128/334 R |
| 4,345,600 A | 8/1982 | Rothfuss | 128/334 R |
| 4,368,736 A | 1/1983 | Kaster | 128/334 C |
| 4,474,181 A | 10/1984 | Schenck | 128/334 R |
| 4,523,592 A | 6/1985 | Daniel | 128/334 C |
| 4,587,202 A | 5/1986 | Borysko | 430/320 |
| 4,657,019 A | 4/1987 | Walsh et al. | 128/334 C |
| 4,676,245 A | 6/1987 | Fukuda | 128/334 C |
| 4,681,110 A | 7/1987 | Wiktor | 128/343 |
| 4,747,407 A | 5/1988 | Liu et al. | 128/334 R |
| 4,777,096 A | 10/1988 | Borysko | 428/571 |
| 4,787,386 A | 11/1988 | Walsh et al. | 128/334 R |
| 4,872,874 A | 10/1989 | Taheri | 623/1 |
| 4,873,975 A | 10/1989 | Walsh et al. | 128/334 R |
| 4,899,744 A | 2/1990 | Fujitsuka et al. | 606/153 |
| 4,930,502 A | 6/1990 | Chen | 606/150 |
| 4,930,674 A | 6/1990 | Barak | 227/179 |
| 4,950,283 A | 8/1990 | Dzubow et al. | 606/216 |
| 4,957,499 A | 9/1990 | Lipatov et al. | 606/153 |
| 4,979,954 A | 12/1990 | Gwathmey et al. | 606/219 |
| 4,997,439 A | 3/1991 | Chen | 606/216 |
| 5,035,702 A | 7/1991 | Taheri | 606/153 |
| 5,037,428 A | 8/1991 | Picha et al. | 606/155 |
| 5,057,401 A | 10/1991 | Borysko et al. | 430/320 |
| 5,078,735 A | 1/1992 | Mobin-Uddin | 623/1 |
| 5,089,008 A | 2/1992 | Chen | 606/216 |
| 5,123,908 A | 6/1992 | Chen | 606/153 |
| 5,188,638 A | 2/1993 | Tzakis | 606/153 |
| 5,234,447 A | 8/1993 | Kaster et al. | 606/153 |
| 5,250,057 A | 10/1993 | Chen | 606/153 |
| 5,263,973 A | 11/1993 | Cook | 606/216 |
| 5,336,233 A | 8/1994 | Chen | 606/153 |
| 5,346,501 A | 9/1994 | Regula et al. | 605/151 |
| 5,366,462 A | 11/1994 | Kaster et al. | 606/153 |
| 5,403,333 A | 4/1995 | Kaster et al. | 606/151 |
| 5,456,714 A * | 10/1995 | Owen | 623/1.31 |
| 5,486,187 A | 1/1996 | Schenck | 606/153 |
| 5,501,689 A | 3/1996 | Green et al. | 606/139 |
| 5,562,690 A | 10/1996 | Green et al. | 606/154 |
| 5,653,743 A | 8/1997 | Martin | 623/1 |
| 5,683,453 A | 11/1997 | Palmaz | 623/1 |
| 5,693,454 A | 12/1997 | Munoz | 430/320 |
| 5,695,504 A | 12/1997 | Gifford, III et al. | 606/153 |
| 5,702,048 A | 12/1997 | Eberlin | 227/177.1 |
| 5,707,380 A | 1/1998 | Hinchliffe et al. | 606/153 |
| 5,741,274 A | 4/1998 | Lenker et al. | 606/142 |
| 5,752,966 A | 5/1998 | Chang | 606/151 |
| 5,762,811 A | 6/1998 | Munoz | 216/11 |
| 5,792,180 A | 8/1998 | Munoz | 606/223 |
| 5,868,763 A | 2/1999 | Spence et al. | 606/153 |
| 5,879,371 A | 3/1999 | Gardiner et al. | 606/224 |
| 5,904,697 A | 5/1999 | Gifford, III et al. | 606/155 |
| 5,938,696 A | 8/1999 | Goicoechea et al. | 623/1 |
| 5,957,973 A | 9/1999 | Quiachon et al. | 623/1 |
| 5,976,159 A | 11/1999 | Bolduc et al. | 606/142 |
| 5,976,178 A | 11/1999 | Goldsteen et al. | 623/1 |
| 6,030,392 A | 2/2000 | Dakov | |
| 6,036,703 A * | 3/2000 | Evans et al. | 606/153 |
| 6,068,637 A | 5/2000 | Popov et al. | 606/159 |
| 6,152,937 A | 11/2000 | Peterson et al. | 606/153 |
| 6,176,413 B1 | 1/2001 | Heck et al. | 227/176.1 |
| 6,179,849 B1 | 1/2001 | Yencho et al. | 606/153 |
| 6,254,617 B1 * | 7/2001 | Spence et al. | 606/153 |
| 6,254,618 B1 * | 7/2001 | Dakov | 606/153 |
| 6,419,681 B1 * | 7/2002 | Vargas et al. | 606/153 |
| 6,461,320 B1 * | 10/2002 | Yencho et al. | 604/8 |
| 6,524,322 B1 * | 2/2003 | Berreklouw | 606/153 |
| 2002/0082625 A1 * | 6/2002 | Huxel et al. | 606/153 |

\* cited by examiner

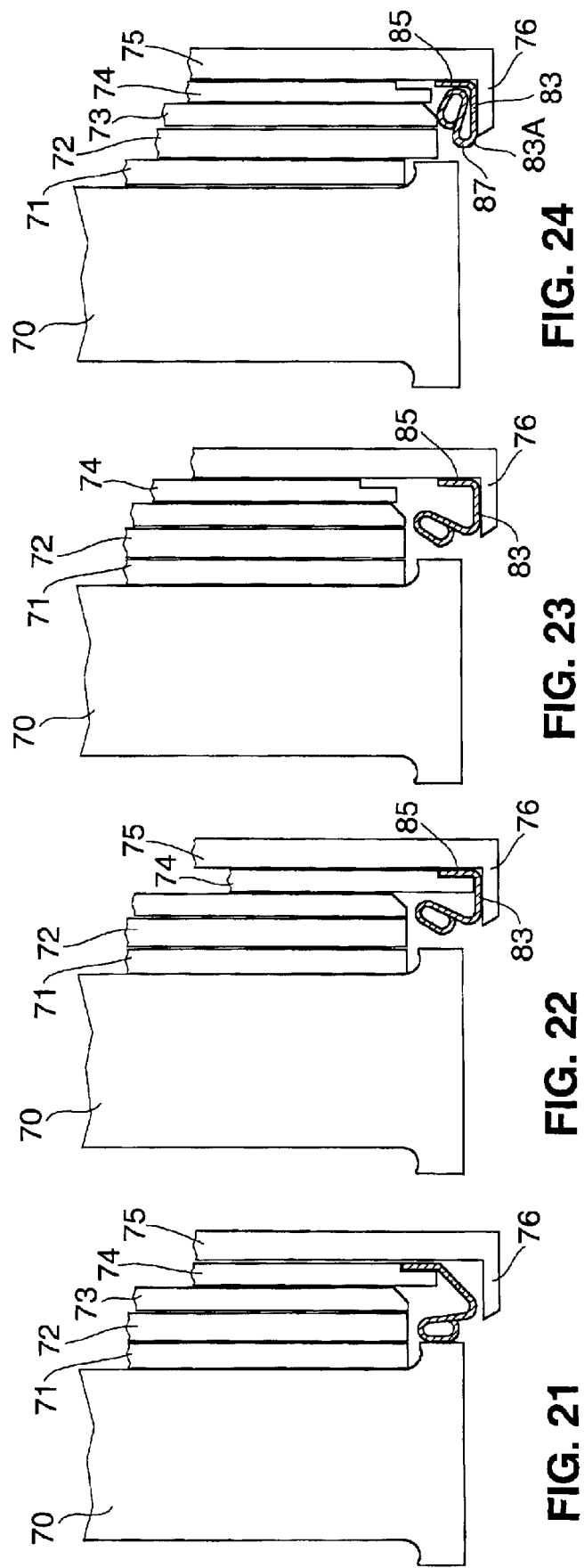

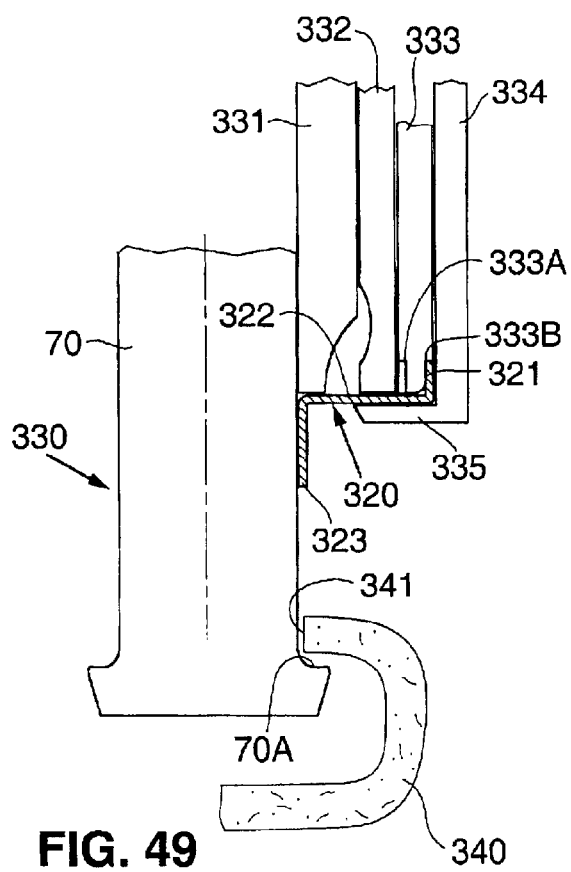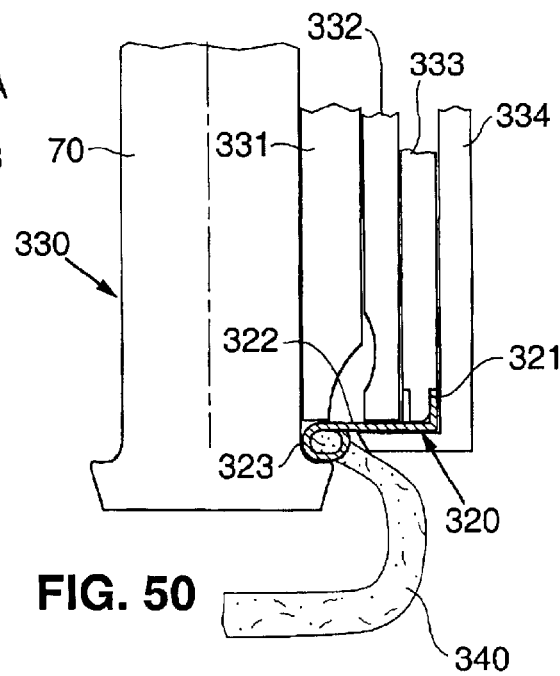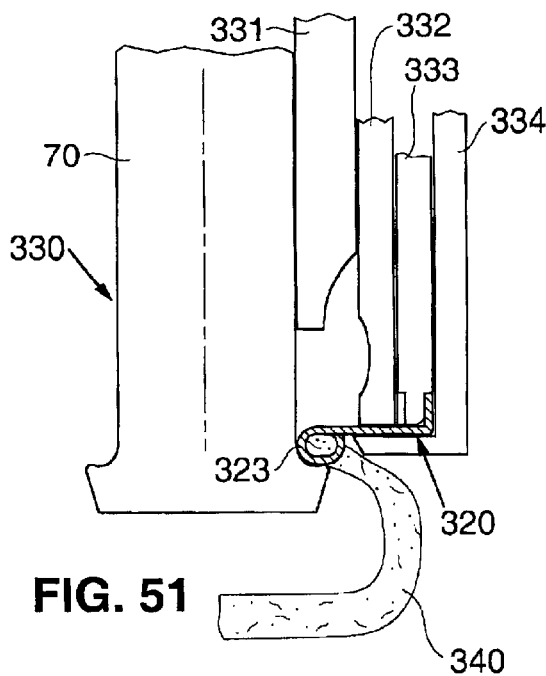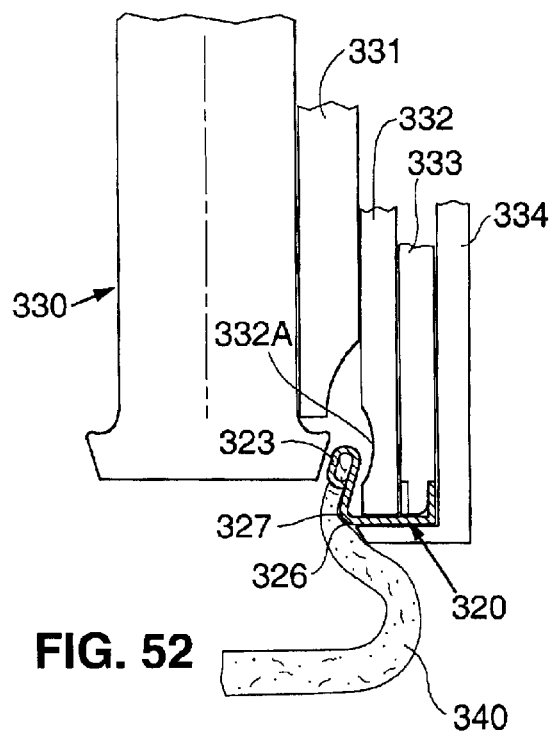
FIG. 49
FIG. 50
FIG. 51
FIG. 52

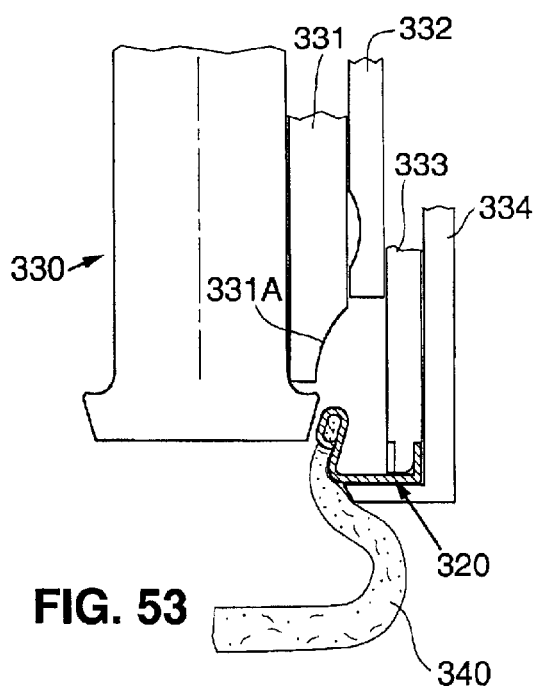
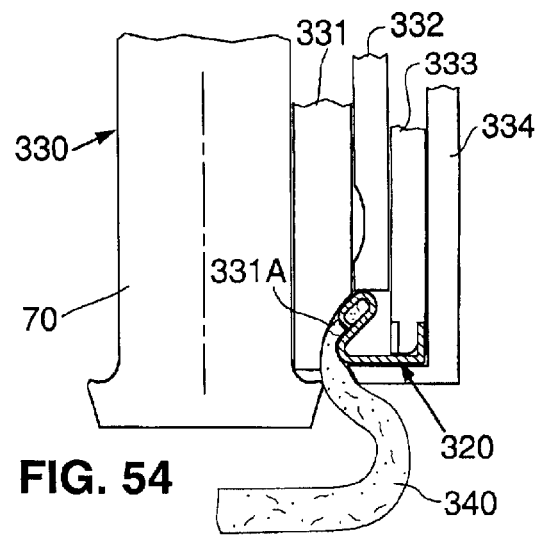
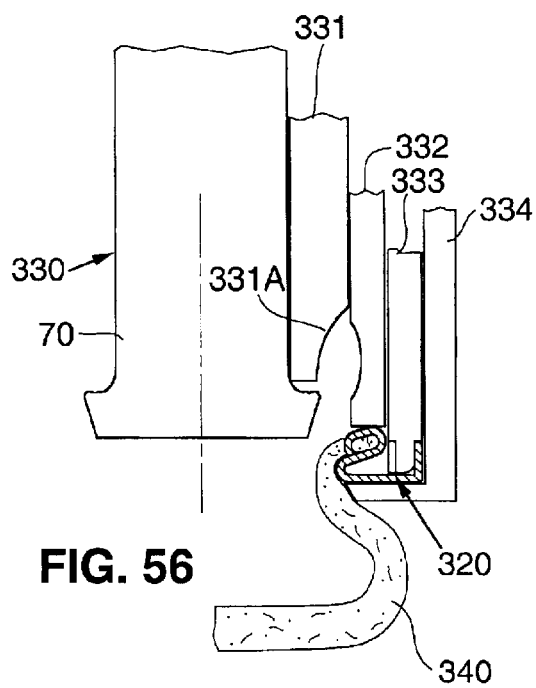
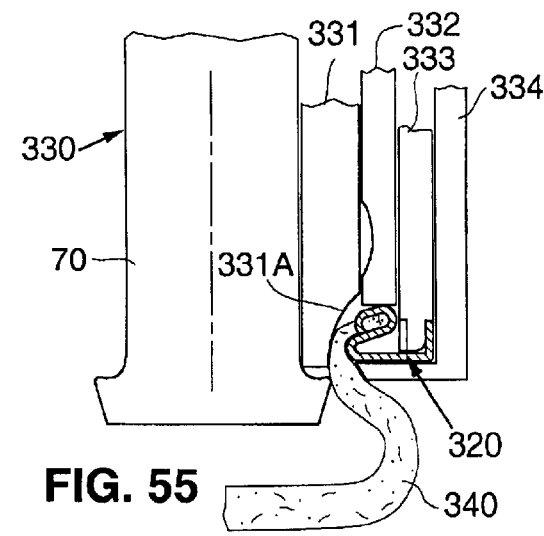
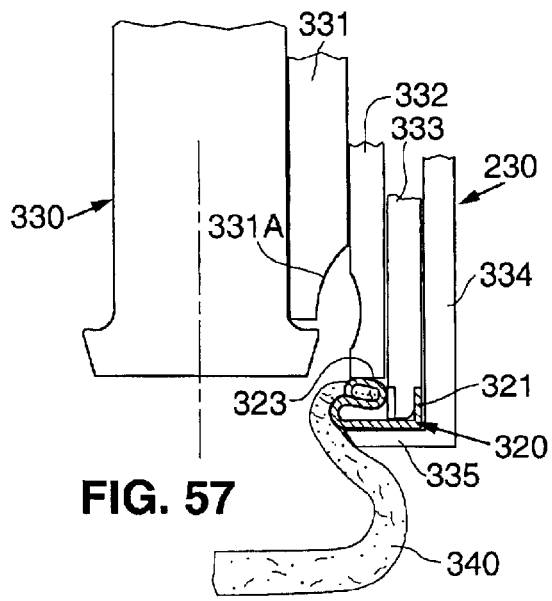

METHOD AND APPARATUS FOR PERFORMING ANASTOMOSIS USING RING HAVING TINES WITH WEAK SECTIONS

TECHNICAL FIELD OF THE INVENTION

The present invention relates to apparatus and methods for performing anastomosis without hand-suturing.

BACKGROUND OF THE INVENTION

In the United States, many coronary artery bypass graft (CABG) procedures are performed on patients annually. Each of these procedures may include one or more graft vessels which are hand sutured. Until recently, coronary artery bypass procedures have been performed with the patient on cardiopulmonary bypass while the heart is stopped with cardioplegia and the surgery is performed on an exposed, stationary heart. Interest in developing a minimally invasive CABG procedure is increasing.

A few pioneering surgeons are now performing minimally invasive procedures in which a coronary artery bypass is performed through a small incision in the chest wall, sometimes on a beating heart, i.e., without heart-lung bypass and cardioplegia.

Until recently all bypass graft procedures have been performed by hand suturing the tiny vessels together with extremely fine sutures under magnification. There is a need (which is addressed by the present invention) for methods and apparatus useful for performing anastomosis during CABG surgery on a beating heart, without hand-suturing.

The present invention can be used to perform end-to-end anastomosis (in which the open end of a vessel or other organ is attached to (and in fluid communication with) the open end of another vessel or other organ without hand-suturing, end-to-side anastomosis (in which the open end of one vessel or other organ is attached to the side wall of a second organ in fluid communication with an incision or other orifice in the second organ's side wall) without hand-suturing, or side-to-side anastomosis (in which incisions or other orifices in the side walls of two vessels or other organs are aligned in fluid communication with each other and the aligned tissue is attached together) without hand-suturing.

SUMMARY OF THE INVENTION

In a class of embodiments, the invention is a ring (for use in anastomosis) that is integrally formed from metal, and includes a central ring portion and tines (and typically also docking features or fastener elements) that extend from the ring portion. In some preferred embodiments, the tines are malleable tines which are movable relative to the ring portion from an initial configuration into a final configuration in which they can grab tissue of an organ (around an incision or other orifice in the organ) and hold such tissue in an everted state. In some preferred embodiments, each tine has a weak section at which it preferentially folds or buckles when subjected to bending force. The ring portion can be rigid or malleable. In preferred embodiments, the ring has a tubular central portion. In other embodiments, the central ring portion is flat (rather than tubular). In some embodiments, the ring is not integrally formed from metal. For example, in some variations, it is assembled from component parts which are connected together (e.g., by welding), or is made of material (other than metal) which has the required mechanical properties.

Another aspect of the invention is a method for installing the ring at an incision or other orifice in a vessel (or other organ) with the ring portion extending around the incision or other orifice. In such method, the tines are advanced against an anvil so that they grab the tissue around the orifice and curl radially (inward or outward) against the anvil (in some embodiments the tines pierce the tissue before they begin to curl; in other embodiments the tines begin to curl before they grab the tissue).

The term "grab" is used herein in a broad sense to denote any operation of grabbing, gripping, grasping, or otherwise capturing the relevant tissue (such that the captured tissue can be moved by moving the thing which captures the tissue), and to denote either "grab and pierce" or "grab without piercing."

The anvil is then retracted to fold (or buckle) the tines so that their curled ends move radially outward. In an optional final step (which is included in preferred embodiments), the tool is used to further fold or bend the tines so that their curled ends move further radially outward. The folding (or buckling), curling, and optional bending of the tines everts the tissue near the orifice edges to expose the inside surface of the organ (so that such exposed inside surface can be joined to tissue of another vessel or organ). In typical use, the ring is installed with the ring portion extending around an incision in the side wall of a blood vessel, and the action of curling the tines everts the incised edges of the orifice to expose the inside lining (intima) of the blood vessel.

In other embodiments, the invention is a tool for installing an anastomosis ring in an incision (or other orifice) in a vessel or other organ. The tool includes an anvil and a set of concentric, independently movable sleeves around the anvil. Each sleeve, and preferably also the anvil, can be advanced (in a distal direction) and retracted (in a proximal direction) when desired relative to the other elements of the tool. In some preferred embodiments the tool has four independently movable sleeves; in other embodiments it has five independently movable sleeves. It is contemplated that the multiple movements of the various sleeves can be automated and synchronized to some degree such that the installation process requires a minimal number of operator manipulations of the installation tool.

Preferably, the distal end of one of the sleeves has two or more circular (or oblong) slots, each for receiving a tubular central ring portion of an anastomosis ring. Thus, the tool can be used to install a relatively small diameter ring (whose central ring portion fits in an innermost slot) or a relatively large diameter ring (whose central ring portion fits in an outermost slot).

In some preferred embodiments, the outermost sleeve is configured to receive a removable flat member (sometimes referred to herein as a disk). The disk has an open center and is oblong or annular, is preferably made of thin metal, and functions during ring installation to provide a surface against which the ring (and tissue engaged therewith) is pressed to deform (fold and/or bend) the ring into its final configuration. When the ring is installed in its final configuration, the disk is released from the installation tool. The tool is then removed from the installed ring, leaving the disk in engagement with the ring and held between the ring and the adjacent tissue.

In other embodiments, the invention is a ring (for use in anastomosis) including a central ring portion (preferably a tubular central ring portion), and tines and fastener elements that extend from the ring portion. Preferably, each tine has a weak section at which it preferentially folds or buckles when subjected to bending force. The ring portion can be rigid or malleable. The fastener elements can be (or include)

malleable elements, spring elements, or both. The fastener elements are used to fasten together two precisely aligned anastomosis rings, each installed in an incision (or other orifice) of a different vessel or other organ, and optionally also to align the two rings together. In preferred embodiments, the fastener elements of one ring are spring elements having a locking configuration in which they exert spring force on fastener elements of another ring to clamp the two rings together.

In other embodiments, the invention is a method for performing an anastomosis, including the steps of installing an anastomosis ring in an incision (or other orifice) in a vessel or other organ, installing another anastomosis ring in an incision (or other orifice) in another vessel or other organ, precisely aligning the two installed anastomosis rings, and fastening the aligned rings together.

BRIEF DESCRIPTION OF THE DRAWING FIGURES

Figure 10:
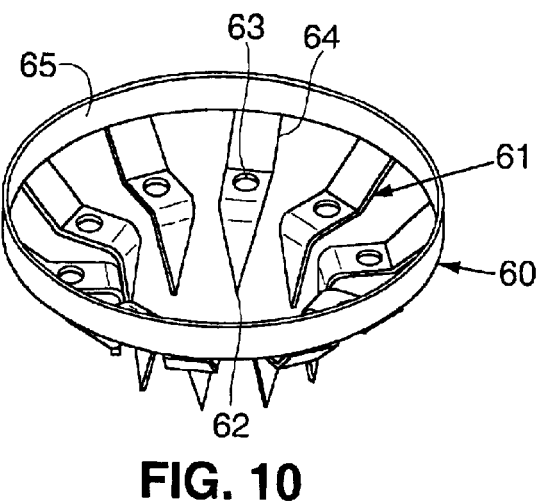
FIG. 10 is a perspective view of an embodiment of the inventive anastomosis ring, with its tines (61) in their initial configuration.
Figure 11:
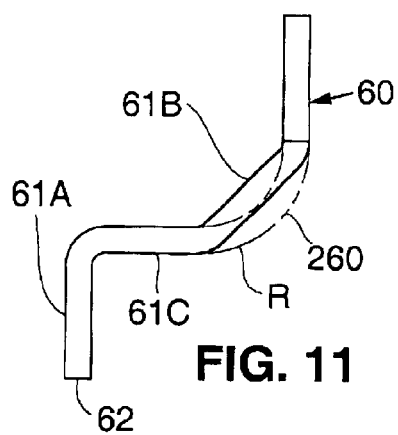

FIG. 11 is a side cross-sectional view of a portion of ring 60 of FIG. 10, and of a portion (shown in phantom view) of another ring (identified by reference numeral 260) which is a variation on ring 60.

Figure 12:
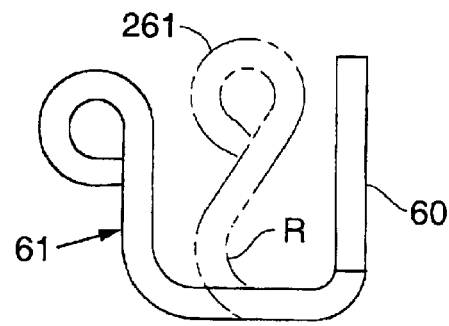

FIG. 12 is a side cross-sectional view of portions of rings 60 and 260 of FIG. 11, after the tines thereof have been curled and formed in accordance with the invention.

Figure 13:
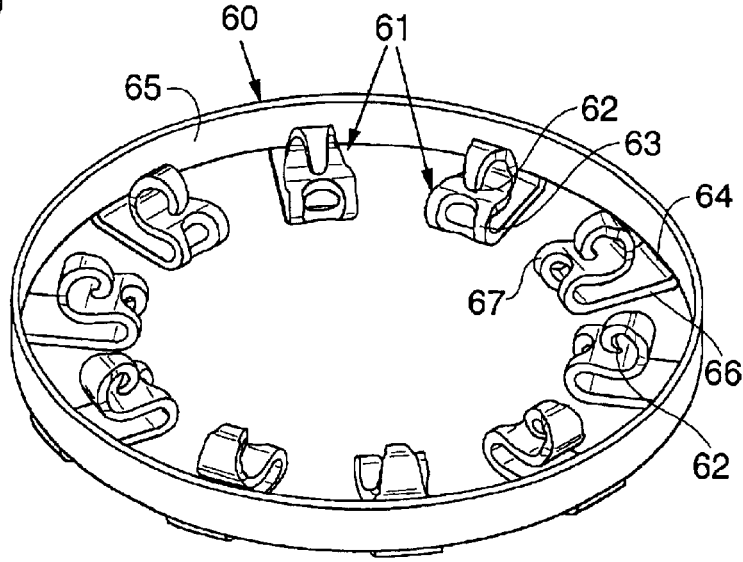

FIG. 13 is a perspective view of the ring of FIG. 10, with each of its tines 61 in its final configuration.

Figure 14:
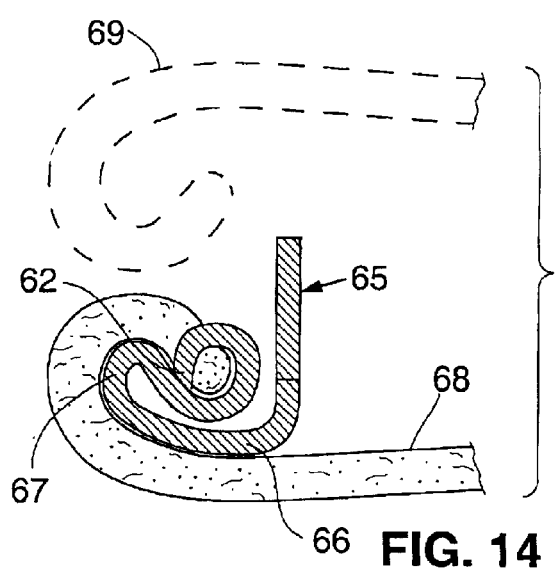

FIG. 14 is a side cross-sectional view of a portion of ring 60 (with one tine 61 in the FIG. 13 configuration) installed in tissue of a first vessel at the edge of an incision, and a second vessel (shown in phantom view) aligned with the first vessel.

Figure 15:
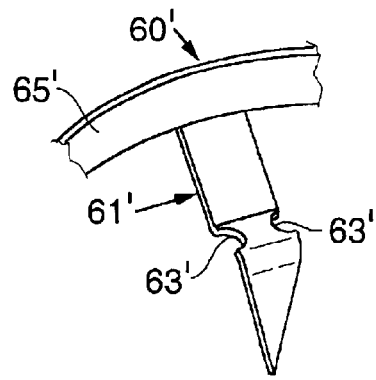

FIG. 15 is a perspective view of a portion of a variation on ring 60 of FIG. 10, with one of its tines (61') in its initial configuration.

Figure 16:
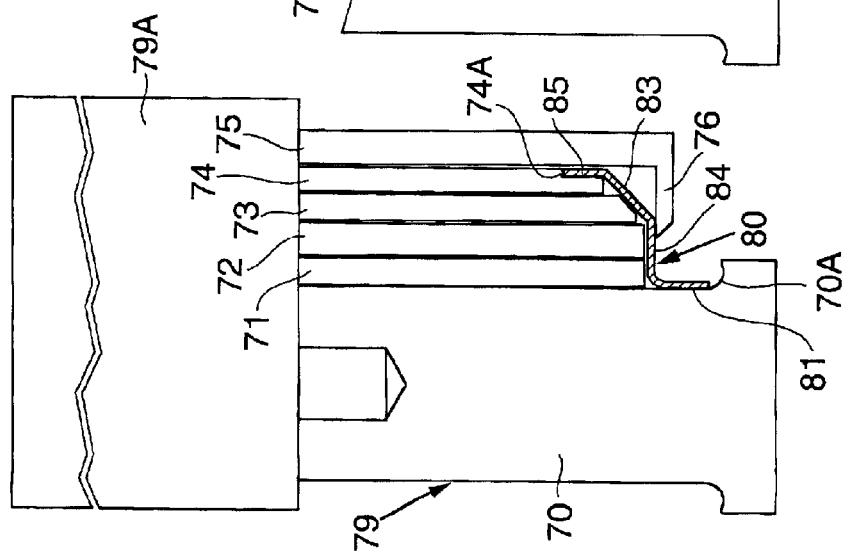

FIG. 16 is a side cross-sectional view of a portion of an embodiment (80) of the inventive ring and a portion of a tool (79) for installing this ring, in the configuration in which they would be at an early stage (to be referred to as a "first" stage) of installing the ring around an opening of an organ.

Figure 17:
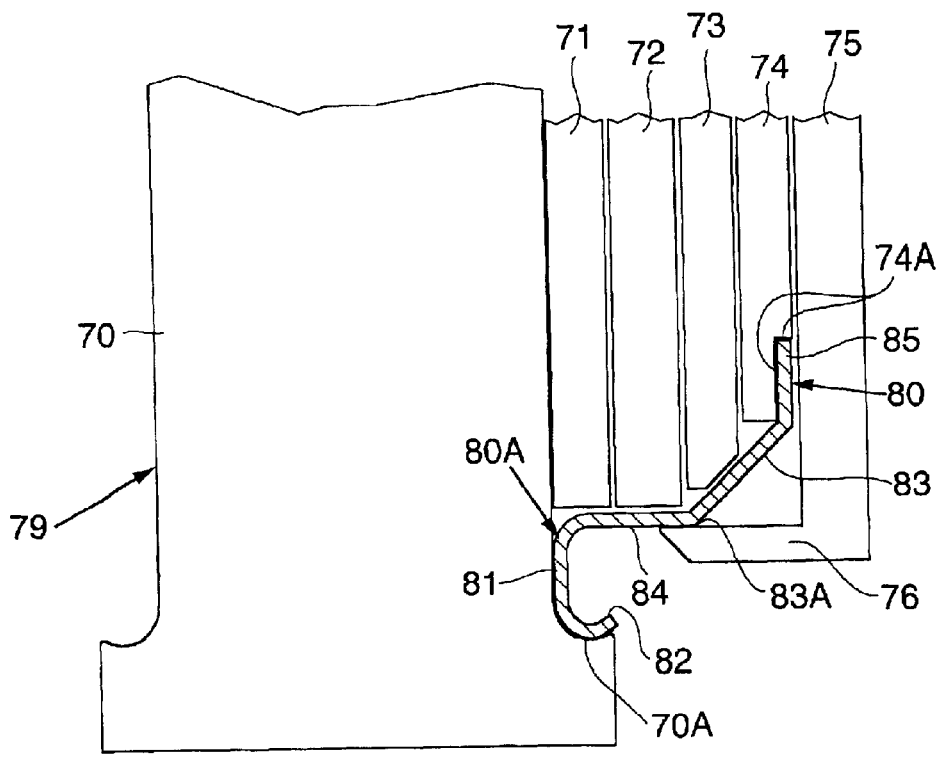

FIG. 17 is a side cross-sectional view of ring 80 and tool 79 of FIG. 16, in the configuration in which they would be at a second stage of installing the ring around an opening of an organ.

Figure 18:
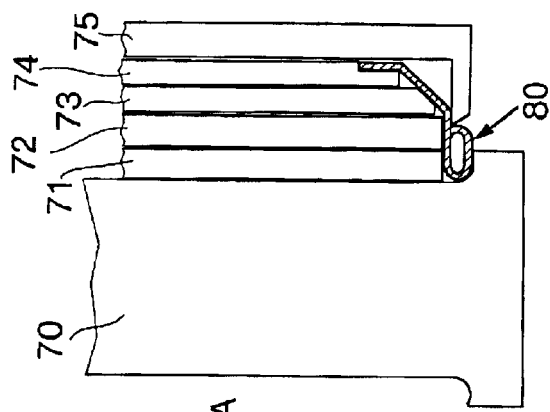

FIG. 18 is a side cross-sectional view of ring 80 and tool 79 of FIG. 16, in the configuration in which they would be at a third stage of installing the ring around an opening of an organ.

Figure 19:
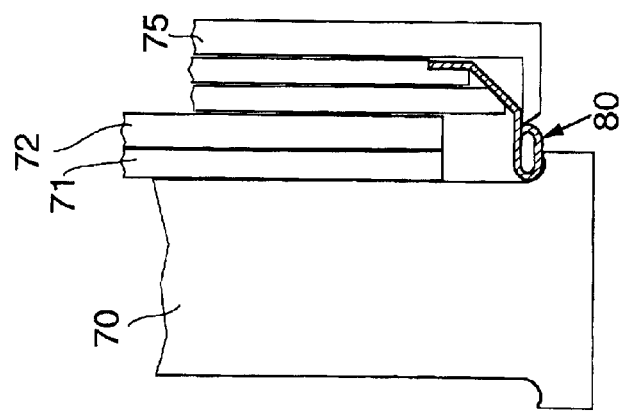

FIG. 19 is a side cross-sectional view of ring 80 and tool 79 of FIG. 16, in the configuration in which they would be at a fourth stage of installing the ring around an opening of an organ.

Figure 20:
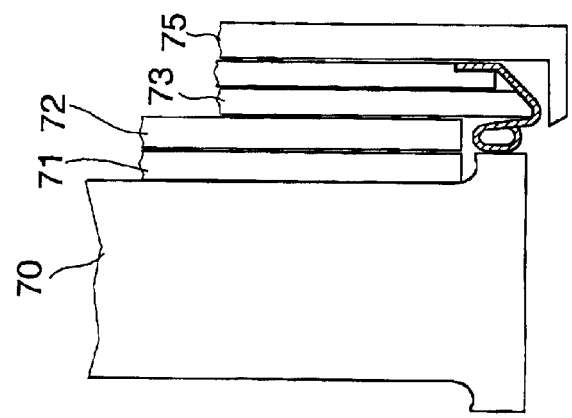

FIG. 20 is a side cross-sectional view of ring 80 and tool 79 of FIG. 16, in the configuration in which they would be at a fifth stage of installing the ring around an opening of an organ.

FIG. 21 is a side cross-sectional view of ring 80 and tool 79 of FIG. 16, in the configuration in which they would be at a sixth stage of installing the ring around an opening of an organ.

FIG. 22 is a side cross-sectional view of ring 80 and tool 79 of FIG. 16, in the configuration in which they would be at a seventh stage of installing the ring around an opening of an organ.

FIG. 23 is a side cross-sectional view of ring 80 and tool 79 of FIG. 16, in the configuration in which they would be at an eighth stage of installing the ring around an opening of an organ.

FIG. 24 is a side cross-sectional view of ring 80 and tool 79 of FIG. 16, in the configuration in which they would be at a ninth stage of installing the ring around an opening of an organ.

Figure 25:
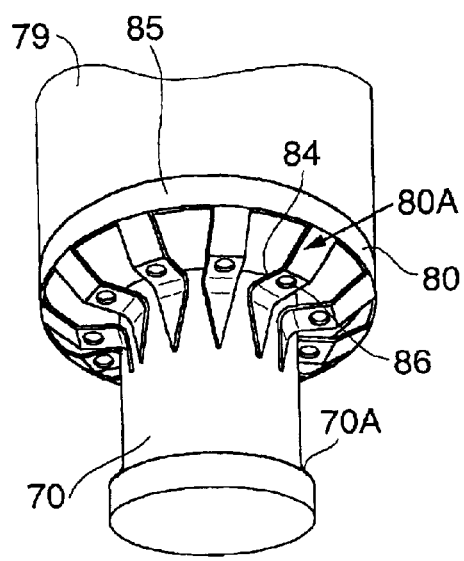

FIG. 25 is a simplified perspective view of the distal end of tool 79 (of FIG. 16), without sleeve 75, and with ring 80 mounted thereon.

Figure 25A:
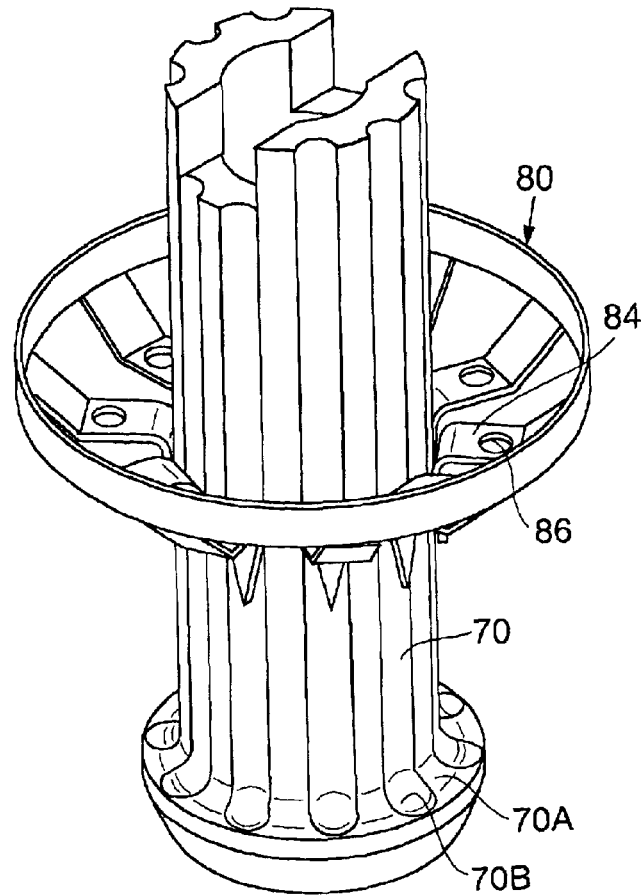

FIG. 25A is a perspective view of ring 80 around a preferred (fluted) implementation of anvil 70.

Figure 26:
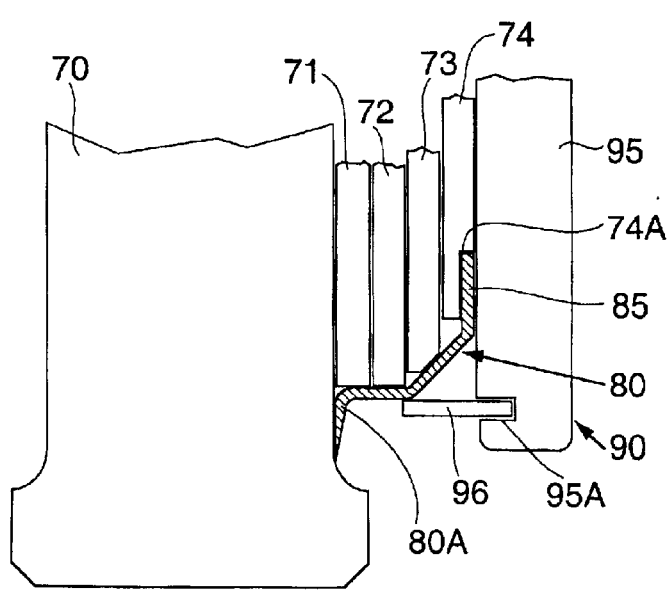

FIG. 26 is side cross-sectional view of a portion of ring 80 of (of FIGS. 16–25) and a portion of another embodiment of the inventive tool (90) for installing this ring around an opening of an organ.

Figure 27:
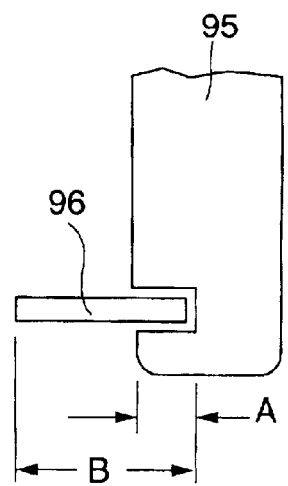

FIG. 27 is a detail view of a portion of the apparatus shown in FIG. 26.

Figure 28:
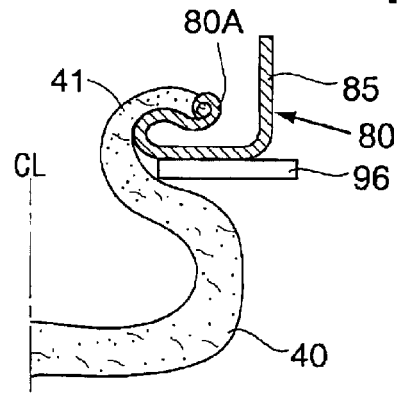

FIG. 28 is a side cross-sectional view of a portion of ring 80 and a portion of tool 90, which have been installed (using tool 90) around an incision 15 in a blood vessel.

Figure 29:
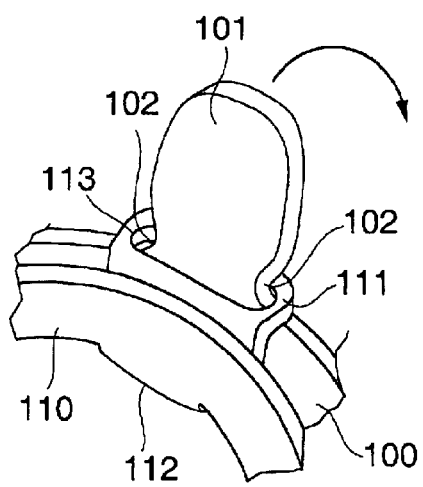

FIG. 29 is a perspective view of portions of two aligned anastomosis rings (rings 100 and 110) having tab fasteners for fastening the rings together.

Figure 30:
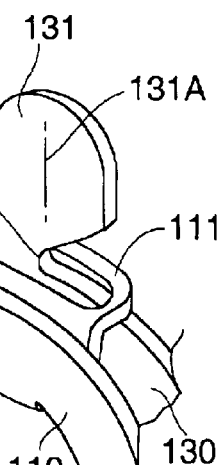

FIG. 30 is a perspective view of a portion of a variation on anastomosis ring 100 (of FIG. 29) having a tab fastener which is a variation on fastener 101 of FIG. 29.

Figure 31:
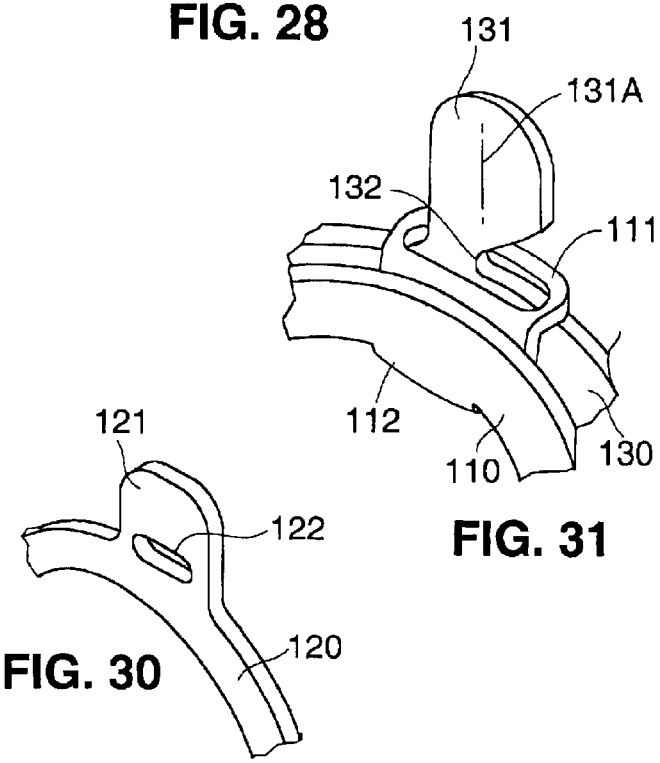

FIG. 31 is a perspective view of portions of two aligned anastomosis rings (rings 130 and 110) having tab fasteners, one of which (tab 131) is a variation on fastener 101 of FIG. 29.

Figure 32:
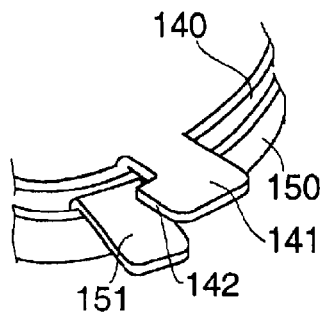

FIG. 32 is a perspective view of portions of two aligned anastomosis rings (rings 140 and 150) having a different type of tab fasteners for fastening the rings together, with the fasteners in an open (unlocked) configuration.

Figure 33:
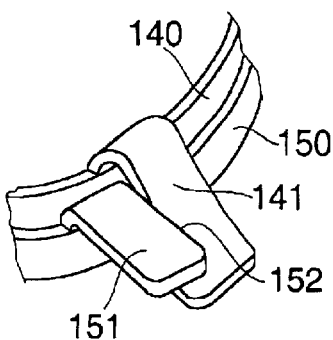

FIG. 33 is a perspective view of the elements shown in FIG. 32, after these elements have been moved relative to each other into a closed (locked) configuration to fasten the rings together.

Figure 34:
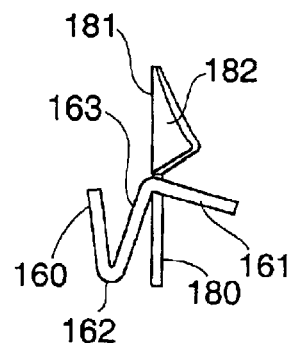

FIG. 34 is a side cross-sectional view of portions of two aligned anastomosis rings (rings 160 and 180) having spring fasteners for fastening the rings together.

Figure 35:
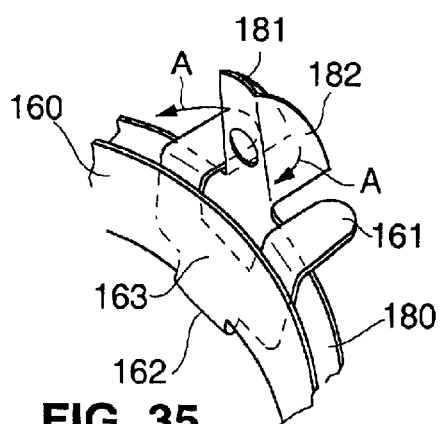

FIG. 35 is a perspective view of portions of the aligned anastomosis rings 160 and 180 shown in FIG. 34.

Figure 36:
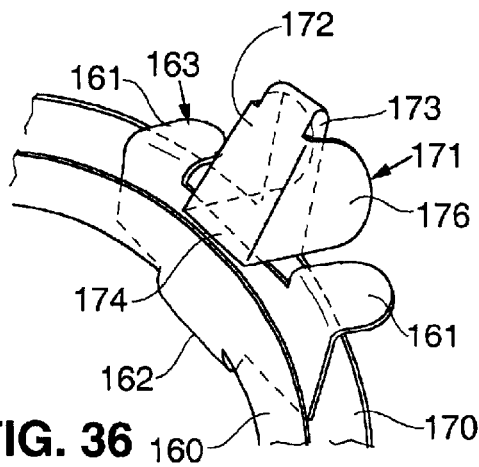

FIG. 36 is a perspective view of portions of two aligned anastomosis rings (rings 160 and 170) having spring fasteners of another type for fastening the rings together.

Figure 37:
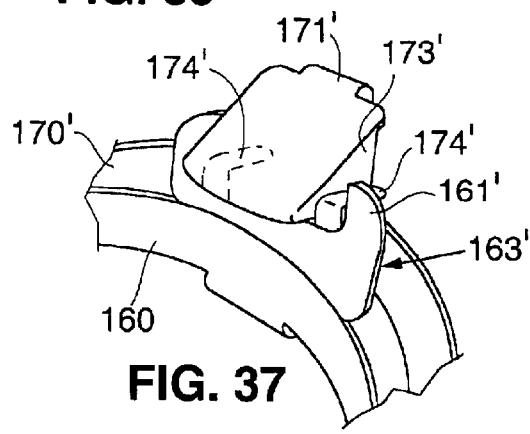

FIG. 37 is a perspective view of a portion of a variation on ring 170 of FIG. 36.

Figure 38:
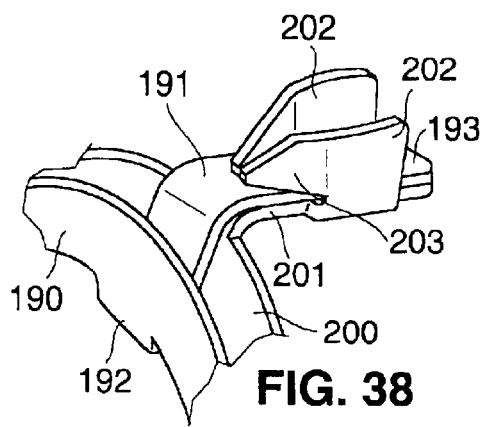

FIG. 38 is a perspective view of portions of two aligned anastomosis rings (rings 190 and 200) having spring fasteners of another type for fastening the rings together.

Figure 39:
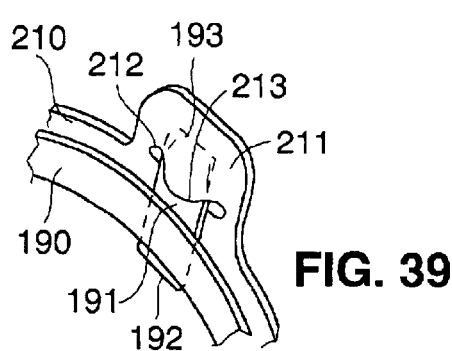

FIG. 39 is a perspective view of portions of two aligned anastomosis rings (rings 190 and 210) having tab fasteners for fastening the rings together, with the fasteners in an unlocked position.

Figure 40:
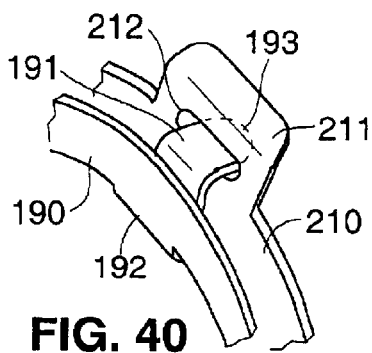

FIG. 40 is a perspective view of portions of aligned rings 190 and 210 of FIG. 39, with the tab fasteners in a locked position.

Figure 41:
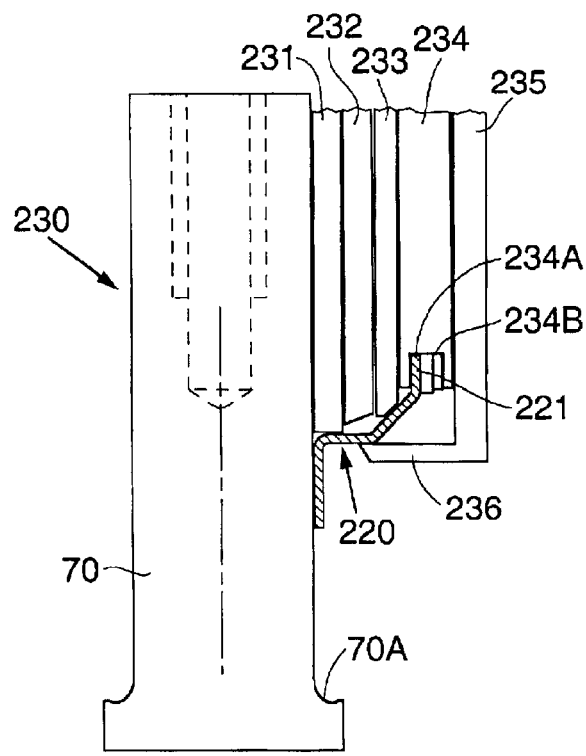

FIG. 41 is a side cross-sectional view of a portion of an embodiment (220) of the inventive ring and a portion of a tool (230) for installing this ring, in the configuration in which they would be at an early stage (to be referred to as a "first" stage) of installing the ring around an opening of an organ.

Figure 42:
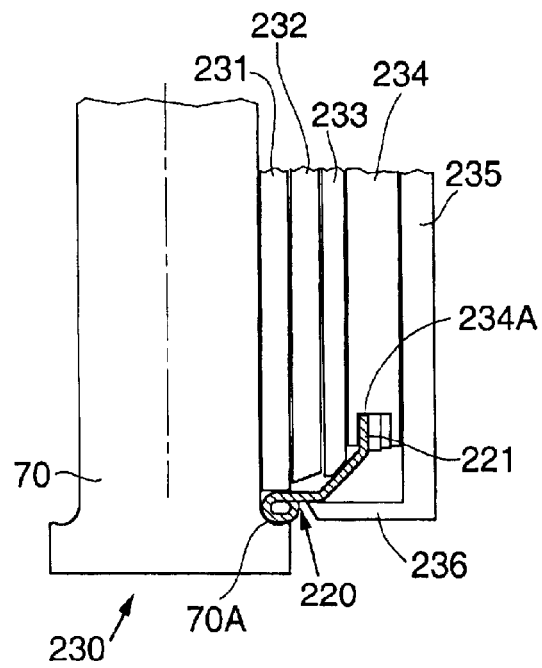

FIG. 42 is a side cross-sectional view of ring 220 and tool 230 of FIG. 41, in the configuration in which they would be at a second stage of installing the ring around an opening of an organ.

Figure 43:
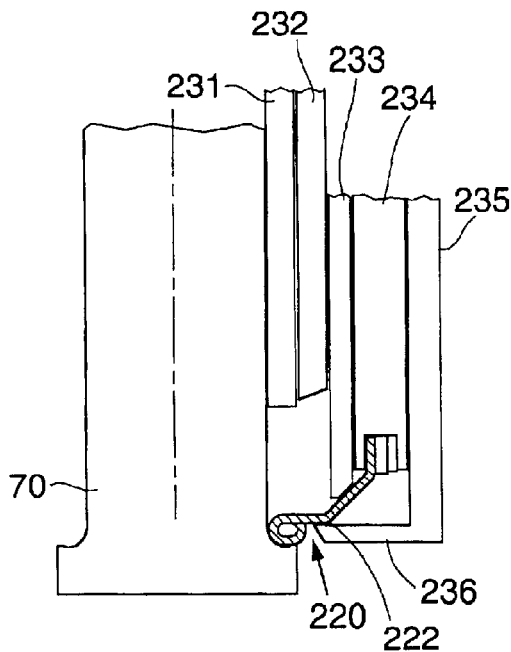

FIG. 43 is a side cross-sectional view of ring 220 and tool 230 of FIG. 41, in the configuration in which they would be at a third stage of installing the ring around an opening of an organ.

Figure 44:
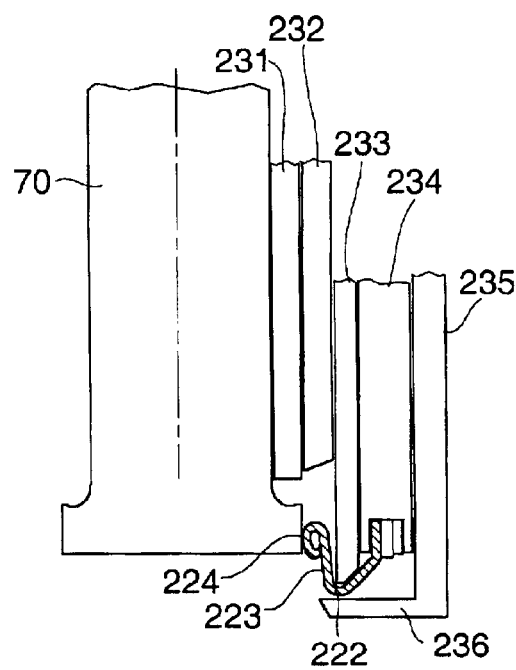

FIG. 44 is a side cross-sectional view of ring 220 and tool 230 of FIG. 41, in the configuration in which they would be at a fourth stage of installing the ring around an opening of an organ.

Figure 45:
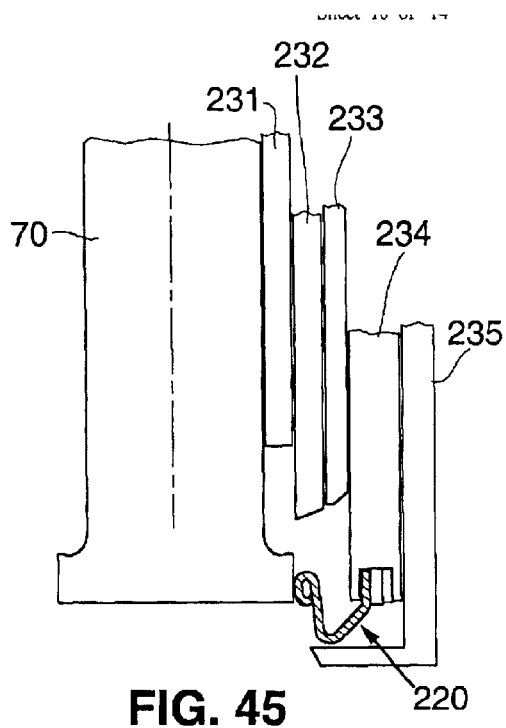

FIG. 45 is a side cross-sectional view of ring 220 and tool 230 of FIG. 41, in the configuration in which they would be at a fifth stage of installing the ring around an opening of an organ.

Figure 46:
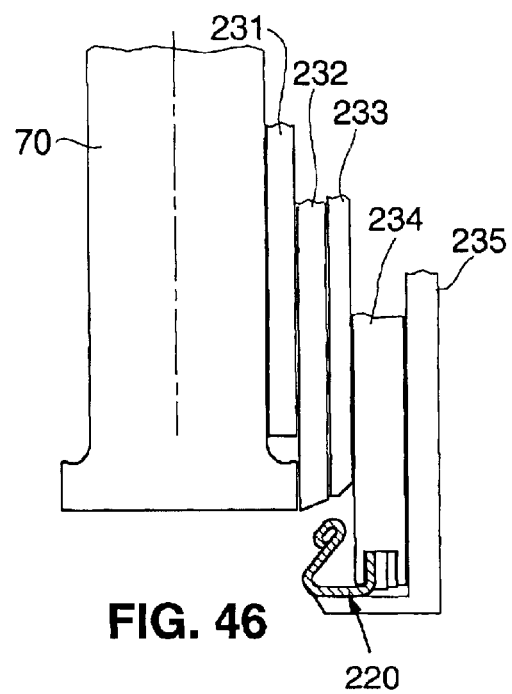

FIG. 46 is a side cross-sectional view of ring 220 and tool 230 of FIG. 41, in the configuration in which they would be at a sixth stage of installing the ring around an opening of an organ.

Figure 47:
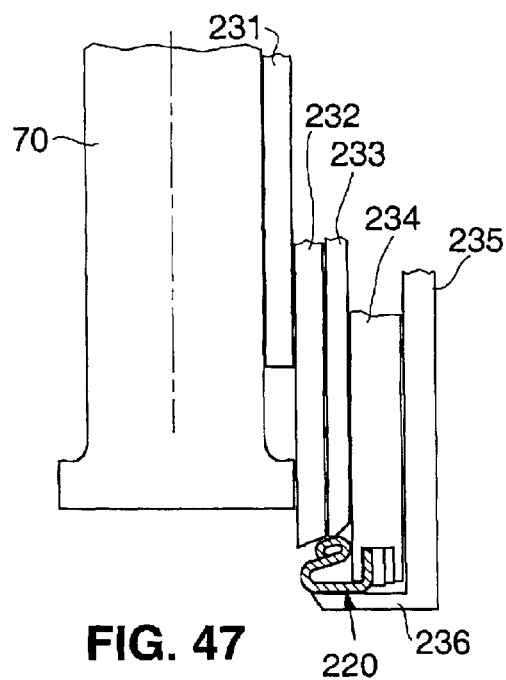

FIG. 47 is a side cross-sectional view of ring 220 and tool 230 of FIG. 41, in the configuration in which they would be at a seventh stage of installing the ring around an opening of an organ.

Figure 48:
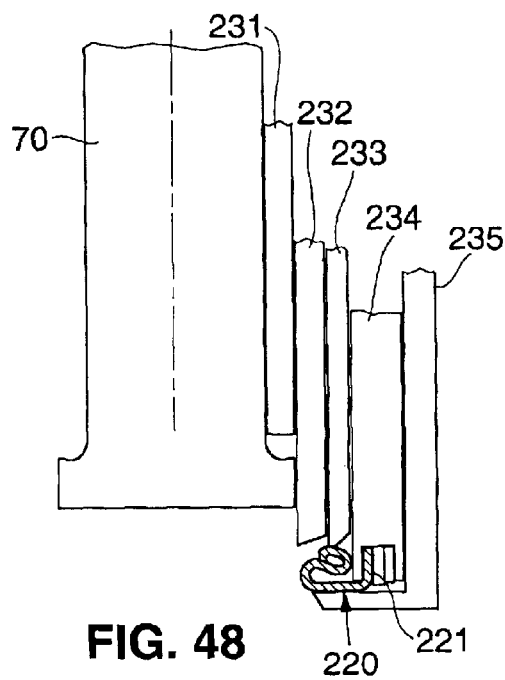

FIG. 48 is a side cross-sectional view of ring 220 and tool 230 of FIG. 41, in the configuration in which they would be at an eighth stage of installing the ring around an opening of an organ.

FIG. 49 is a side cross-sectional view of a portion of an embodiment (320) of the inventive ring and a portion of a preferred embodiment of the inventive tool (330) for installing the ring, in the configuration in which they would be at an early stage (to be referred to as a "first" stage) of installing the ring around an opening of an organ.

FIG. 50 is a side cross-sectional view of ring 320 and tool 330 of FIG. 49, in the configuration in which they would be at a second stage of installing the ring around an opening of an organ.

FIG. 51 is a side cross-sectional view of ring 320 and tool 330 of FIG. 49, in the configuration in which they would be at a third stage of installing the ring around an opening of an organ.

FIG. 52 is a side cross-sectional view of ring 320 and tool 330 of FIG. 49, in the configuration in which they would be at a fourth stage of installing the ring around an opening of an organ.

FIG. 53 is a side cross-sectional view of ring 320 and tool 330 of FIG. 49, in the configuration in which they would be at a fifth stage of installing the ring around an opening of an organ.

FIG. 54 is a side cross-sectional view of ring 320 and tool 330 of FIG. 49, in the configuration in which they would be at a sixth stage of installing the ring around an opening of an organ.

FIG. 55 is a side cross-sectional view of ring 320 and tool 330 of FIG. 49, in the configuration in which they would be at a seventh stage of installing the ring around an opening of an organ.

FIG. 56 is a side cross-sectional view of ring 320 and tool 330 of FIG. 49, in the configuration in which they would be at an eighth stage of installing the ring around an opening of an organ.

FIG. 57 is a side cross-sectional view of ring 320 and tool 330 of FIG. 49, in the configuration in which they would be at an ninth stage of installing the ring around an opening of an organ.

Figure 58:
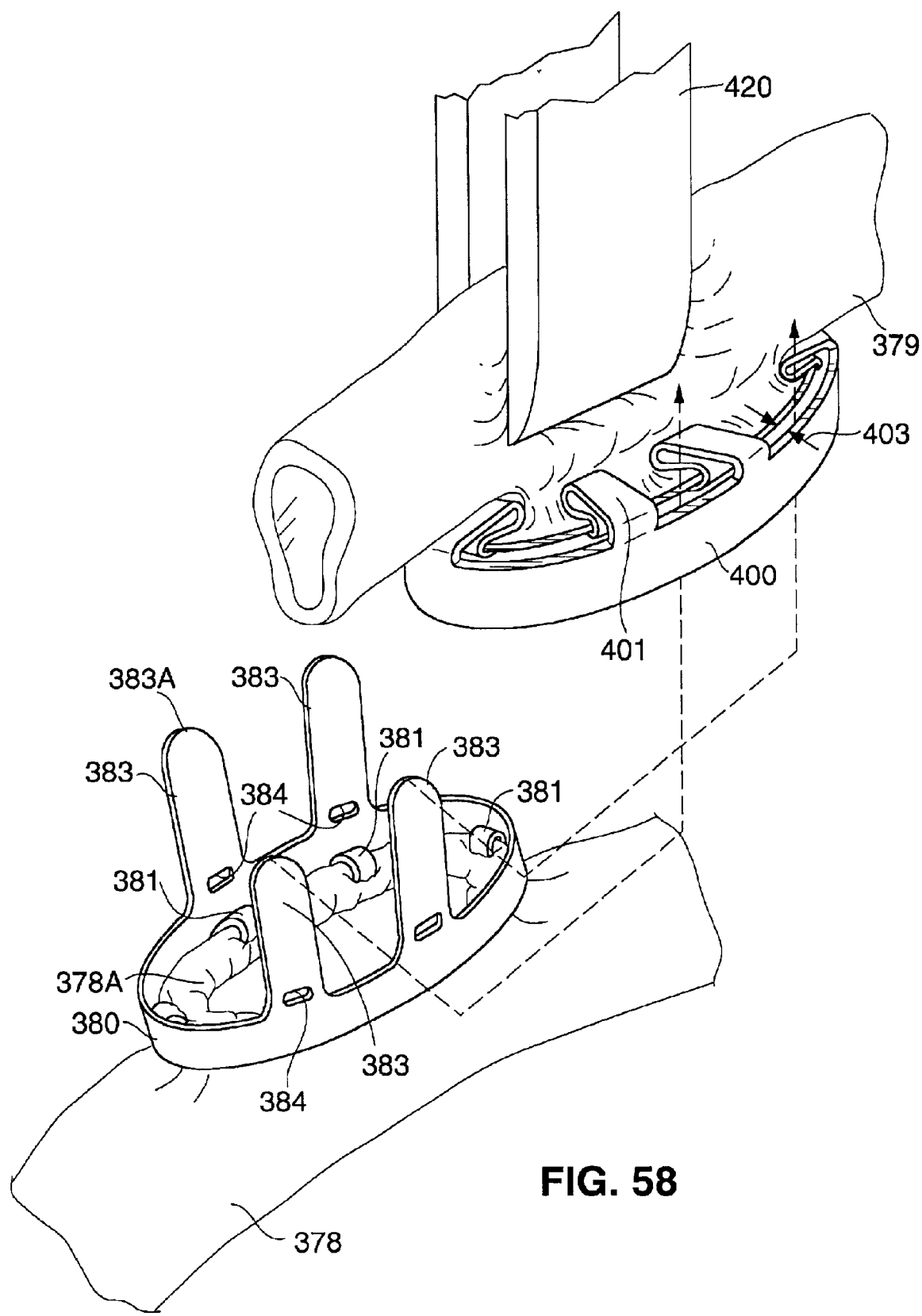

FIG. 58 is a perspective view of two of the inventive anastomosis rings (380 and 400), each installed in an incision in a different blood vessel, and a pair of forceps 420 gripping one of the blood vessels. Rings 380 and 400 are preferred embodiments of the inventive anastomosis rings.

Figure 59:
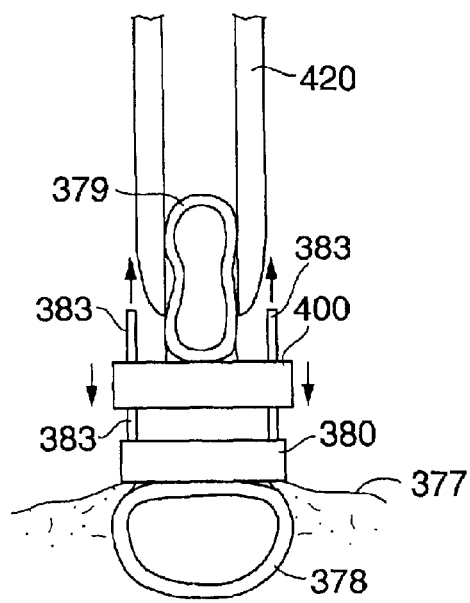

FIG. 59 is a cross-sectional view of the apparatus and tissue of FIG. 58, after ring 400 has been lowered onto docking tabs 383 of ring 380.

Figure 60:
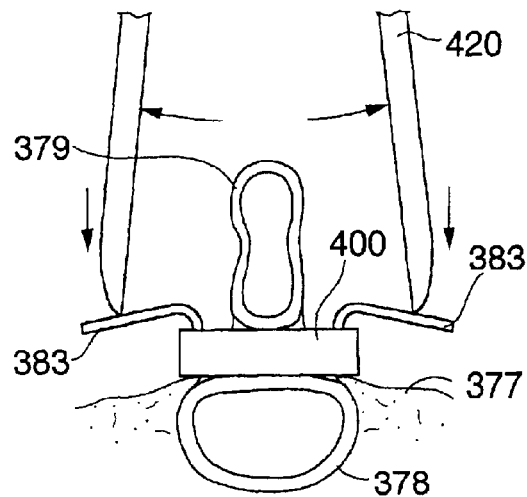
Figure 61:
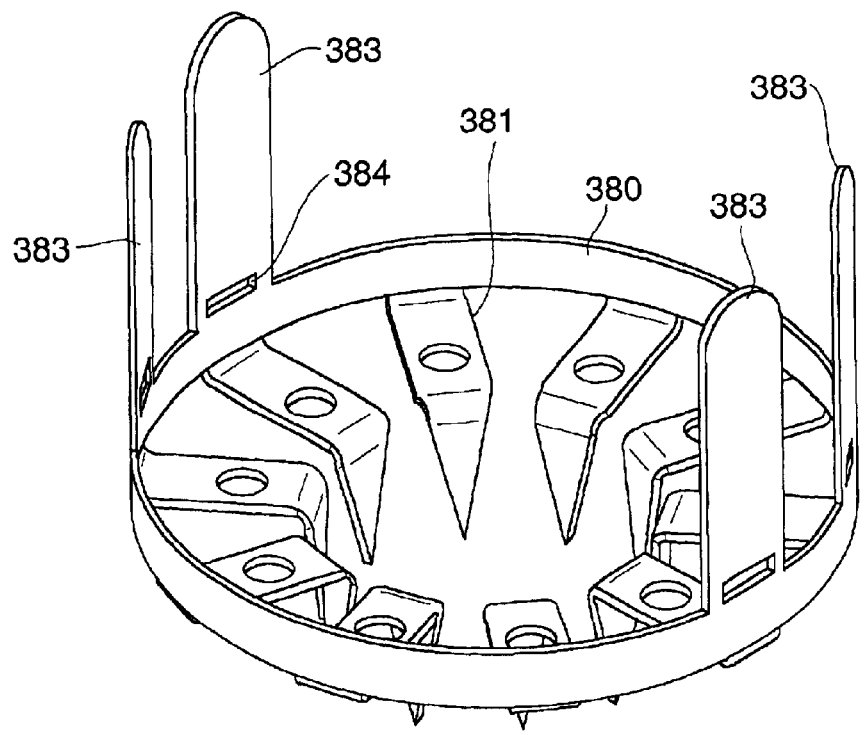

FIG. 60 is a cross-sectional view of the apparatus and tissue of FIG. 59 after rings 380 and 400 have been aligned, while docking tabs 383 are being folded into a locking configuration FIG. 61 is a perspective view of ring 380 of FIG. 58, in its pre-installation configuration.

DETAILED DESCRIPTION OF THE PREFERRED EMBODIMENTS

The expression "malleable" element is used herein to denote an element that, when deformed from a first shape into a second shape, will not relax back into the first shape from the second. A flexible element can be elastic or malleable (the term "flexible" is used in a broad sense encompassing both the narrower terms "malleable" and "elastic").

Figure 1:
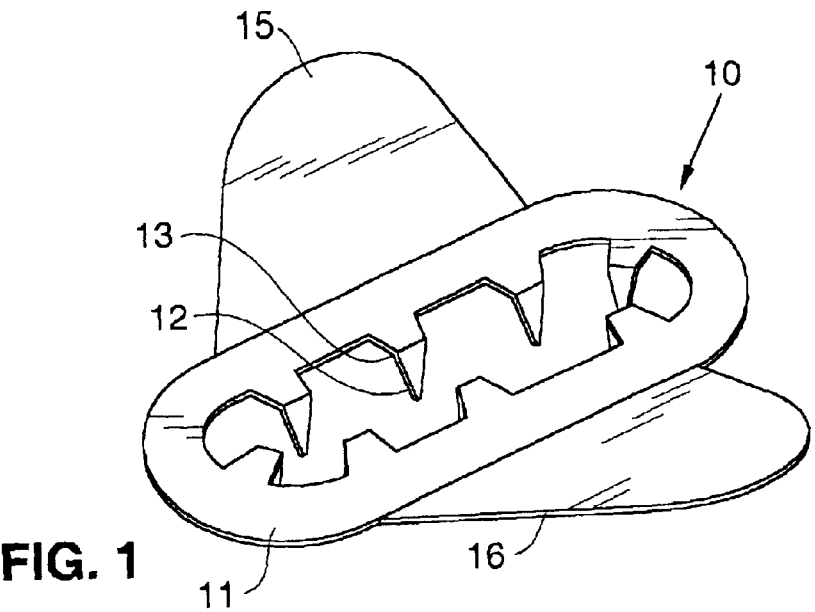
FIG. 1 is a perspective view of an embodiment of the inventive ring for use in performing anastomosis without hand sutures.

FIG. 1 is a perspective view of an anastomosis ring 10, which is an embodiment of the inventive ring for use in performing anastomosis without hand sutures. Ring 10 is integrally formed from metal, and includes a central ring portion 11, and tines 12 and docking features 15 and 16 which extend out from ring portion 11. Preferably, each of docking features 15 and 16 is implemented so as to add stiffness to ring portion 11, and to define at least one snap feature (or other fastener) for using in fastening together ring 10 (after it has been installed in a vessel or other organ) with another anastomosis ring. Tines 12 are malleable. Ring portion 11 can be implemented to be flexible but is preferably rigid. Ring portion 11 is substantially flat in a plane perpendicular to the central axis of ring 10.

Each tine 12 is manufactured to be generally flat, and is then bent so as to define a bent edge 13 between ring portion 11 and a distal tine portion which terminates at a sharp distal end. In the initial configuration, the distal tine portions are oriented at least substantially perpendicularly to the plane of ring portion 11. Each tine 12 is preferably tapered, with its width decreasing from its relatively wide proximal end (at portion 11) to its sharp distal end. Each tine 12 also has a hinge or weak section (sometimes referred to herein as a "weak portion") at a location that is separated from (but typically near to) edge 13. Such weak portions are not labeled in FIG. 1. The number of tines is variable and depends on the size of the ring and the size of the tines. The number should be sufficient to ensure that all of the tissue surrounding the orifice is grasped and everted.

The method for installing ring 10 (and variations thereon) in an opening (e.g., incision) in a vessel or other organ will be described below in detail, but is generally as follows. An anvil is inserted through the opening into the organ, and ring 10 is positioned with the sharp tips of tines 12 contacting the tissue surrounding the opening. An installation tool is then operated to drive tines 12 against the anvil, causing tines 12 to penetrate through the tissue into contact with the anvil and then begin to curl (or to begin to curl against the anvil and then penetrate the tissue as they continue to curl) so as to engage (and grab) the tissue and optionally also to begin to evert the tissue that surrounds the opening. Then, the anvil is retracted through ring portion 11, thereby causing each tine 12 to fold or buckle about its hinge (or weak portion) and thus move into a folded (or buckled) and curled configuration. The tines grab the tissue surrounding the opening and thus evert the incised tissue edges as they fold or buckle in response to action of the anvil. In some cases, additional shaping forces are exerted on the fines to move them from their folded (or buckled) and curled configuration into a final configuration. Retraction of the anvil does not significantly deform ring portion 11 although it does deform tines 12 relative to ring portion 11. When tines 12 have been deformed into their final configuration and the anvil has retracted out of engagement with ring 10, ring 10 is fully installed at the opening of the organ with ring portion 11 surrounding the opening (so that fluid can flow through the opening), ring 10 holding tissue around the opening so as to expose its intima, and docking features 15 and 16 exposed so that features 15 and 16 can be aligned with and fastened to docking features of another ring that has been installed at an incision in (or opening of) another organ to produce an anastomosis that joins the two organs.

Figure 2:
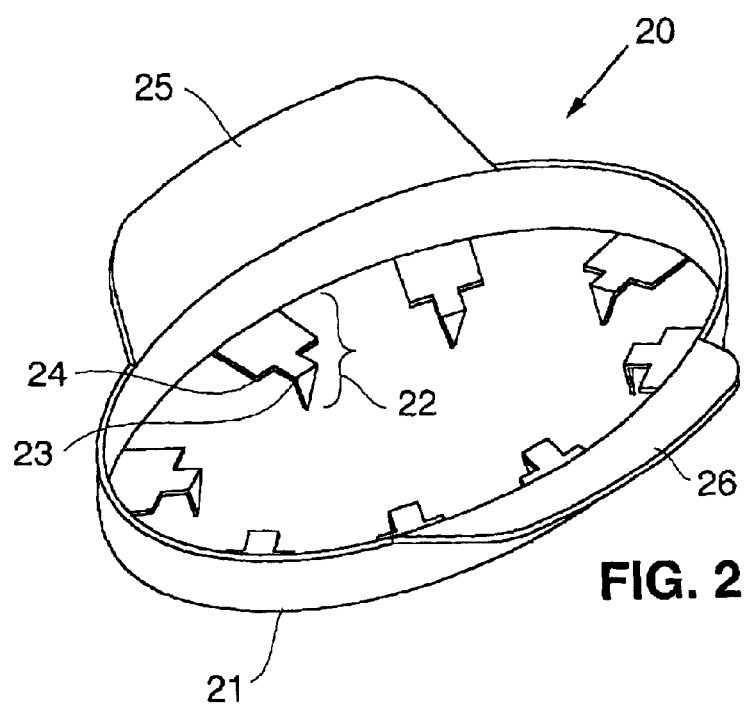
FIG. 2 is a perspective view of another embodiment of the inventive ring for use in performing anastomosis without hand sutures.

FIG. 2 is a perspective view of an anastomosis ring 20, which is another embodiment of the inventive ring for use in performing anastomosis without hand sutures. Ring 20 is integrally formed from metal, and includes a central ring portion 21, and tines 22 and docking features 25 and 26 which extend out from ring portion 21. Ring 20 differs from above-described ring 10 primarily in that its central ring portion 21 is tubular (in the sense that it surrounds a central axis, has substantially greater length (parallel to the central axis) than width (perpendicular to the central axis), and defines a circular or oblong cross-section in a plane perpendicular to the central axis) rather than flat, and in that tines 22 have slightly different shape than tines 12. Tines 22 are malleable. Ring portion 21 can be implemented to be flexible but is preferably rigid.

Figure 3:
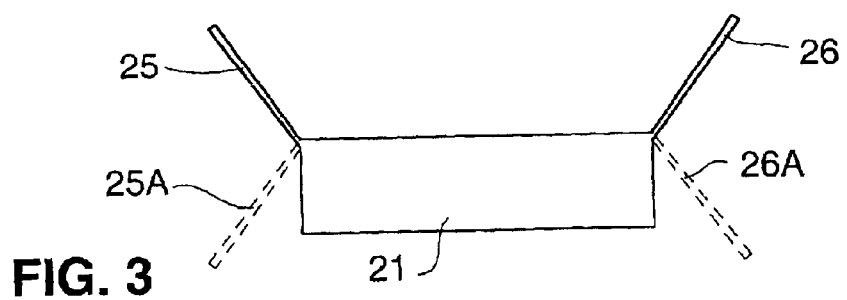
FIG. 3 is a side elevational view of the ring of FIG. 2

Docking features 25 and 26 can be identical to above-described docking features 15 and 16 of FIG. 1. As shown in FIG. 3, features 25 and 26 are bent upward (at an obtuse angle) relative to ring portion 21. Alternatively, the docking features can be bent downward (at an acute angle) relative to ring portion 21, as are alternative docking features 25A and 26A shown in phantom view in FIG. 3.

When two rings 20 (or 10) have been installed, each in an opening of a different organ, an anastomosis to join the organs is accomplished as follows: the two rings are aligned with each other to cause one ring (and the tissue held thereby) to meet the other ring (and the tissue held thereby) such that there is a plane (denoted herein as a "sealing plane") between the two rings; and the aligned rings are then fastened together.

With reference to FIG. 2, each tine 22 of ring 20 is generally flat. Each tine 22 has a relatively wide proximal portion between ring portion 11 and shoulder 24, and a narrower distal portion beyond shoulder 24. Each tine is bent at an edge 23 to define a distal portion (distally beyond edge 23) and a proximal portion (between edge 23 and ring portion 11). Each proximal portion defines a shoulder 24. The width of the distal portion decreases in tapered fashion from edge 23 to a sharp distal end. The distal portions of tines 22 (distal to bent edges 23) are oriented at least substantially perpendicularly to the plane of ring portion 21. During installation, each tine 22 curls tightly from its tip to its edge 23 in response to being advanced against an anvil of an installation tool. Later during installation, each tine 22 tends to fold or buckle at shoulder 24 (rather than at other locations along the tine) in response to retraction of the anvil upward (when viewed as in FIG. 2) through ring portion 21, so that shoulder 24 defines a hinge (or weak portion) of tine 22. In some implementations, each tine 22 also has an additional hinge or weak portion (not labeled) at a location which is separated from (but typically near to) shoulder 24 and separated from edge 23.

More generally, in embodiments of the inventive ring in which each tine (in its pre-installation configuration) has a proximal portion that extends radially inward toward the ring's central axis and a distal portion orientated at least substantially parallel to the ring's central axis (e.g., the embodiments of FIGS. 1 and 2), the distal portion is preferably tapered to its sharp tip to guarantee a tight curl when curling against the anvil of the installation tool during installation. The proximal portion need not be tapered (although the proximal portion of each tine of ring 10 is shown to be tapered in FIG. 1). In typical implementations, the proximal portion of each tine is not tapered (as in FIG. 1) and instead defines a shoulder (e.g., shoulder 24 of each tine of FIG. 2) or other hinge or weak portion (e.g., a hole), so that when the anvil of the installation tool is retracted (so as to fold or buckle the tines radially outward and thereby evert tissue being grabbed by the tines), each tine will preferentially fold or buckle at the shoulder (or other hinge or weak portion) of its proximal portion in response to the force exerted by the retracting anvil.

The method for installing ring 20 (and variations thereon) in an opening (e.g., an incision) in a vessel or other organ will be described below in detail, 1 and is basically the same as the method for installing ring 10. An anvil is inserted through the opening into the organ, and ring 20 is positioned with the sharp tips of tines 22 engaging the tissue surrounding the opening. An installation tool is then operated to drive tines 22 against the anvil, causing tines 22 to penetrate through the tissue into contact with the anvil and then begin to curl (or to begin to curl against the anvil and then penetrate the tissue as they continue to curl) so as to engage (and grab) the tissue and optionally also to begin to evert the tissue that surrounds the opening. Then, the anvil is retracted through ring portion 21, thereby causing each tine 22 to fold or buckle about one or more hinges (or weak portions) thereof and move into a folded (or buckled) and curled configuration. The tines grab the tissue surrounding the opening and thus evert the incised tissue edges as they fold or buckle in response to action of the anvil. In some cases, additional shaping forces are exerted on the tines to move them from their folded (or buckled) and curled configuration into a final configuration. Retraction of the anvil does not significantly deform ring portion 21 although it does deform tines 22 relative to ring portion 21. When tines 22 have been deformed into their final configuration and the anvil has retracted out of engagement with ring 20, ring 20 is fully installed at the opening of the organ with ring portion 21 surrounding the opening (so that fluid can flow through the opening), ring 20 holding tissue around the opening so as to expose its intima, and docking features 25 and 26 exposed.

The tines of each embodiment of the inventive ring (including ring 10 or 20) are preferably wide and flat so that each has a relatively wide surface oriented parallel to the edge of the opening at which the ring is to be installed.

This allows the tines efficiently to exert everting force on the tissue around the opening without tearing or otherwise causing trauma to the tissue, while at the same time the tines can be easily formed in response to exertion of moderate forces thereon (e.g., forces which fold or buckle the tines about their hinges or weak portions).

Figure 4:
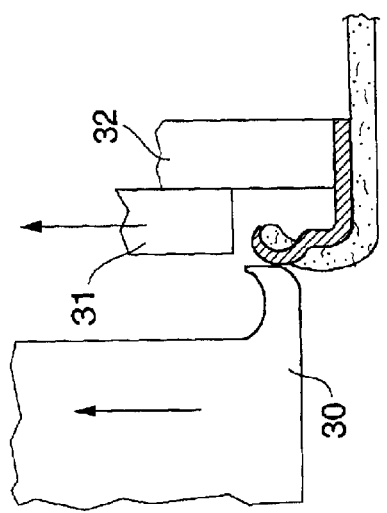
FIG. 4 is a side cross-sectional view of a portion of the ring of FIG. 1 and a portion of an apparatus for installing it, at an early stage of installation of the ring around an incision in the sidewall of a blood vessel.
Figure 5:
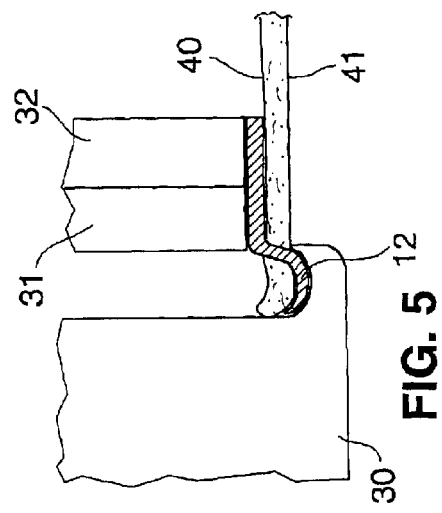
FIG. 5 is a side cross-sectional view of a portion of the ring of FIG. 1 and a portion of an apparatus for installing it, at an intermediate stage of installation of the ring around an incision in the sidewall of a blood vessel.
Figure 6:
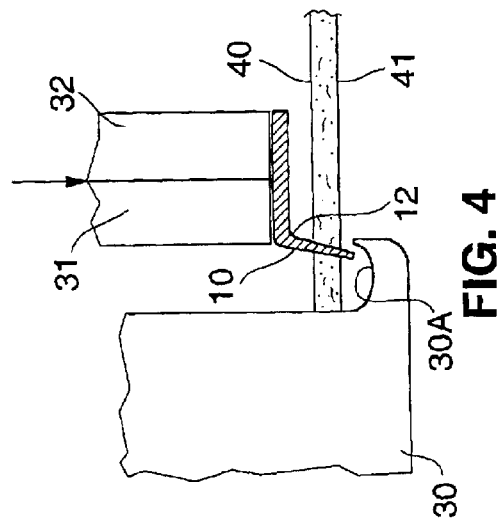
FIG. 6 is a side cross-sectional view of a portion of the ring of FIG. 1 and a portion of an apparatus for installing it, at a late stage of installation of the ring around an incision in the sidewall of a blood vessel.

Ring 10 can be installed using an installation tool comprising anvil 30 and independently translatable sleeves 31 and 32 (as shown in FIGS. 4, 5, and 6) at the site of an incision in the side wall of a blood vessel having exterior surface 40 and interior surface (inside lining or "intima") 41. Only the right half of the distal portion of each of elements 30, 31, and 32, and the right edge of the incision (whose axis of symmetry extends perpendicular to the plane of FIG. 4) are shown in FIGS. 4, 5, and 6. FIG. 4 shows ring 10 and the installation tool at an early stage of the installation process, FIG. 5 shows them at a later stage, and FIG. 6 shows them at a still later stage. When anvil 30 has retracted (upward) into the position shown in FIG. 6, ring 10 has been installed with ring portion 11 extending around the incision, tines 12 grabbing the tissue around the incision, and tines 12 having been deformed so as to evert the incised edges of the tissue to expose the intima 41 of the blood vessel as shown in FIG. 6.

More specifically, as shown in FIG. 4, anvil 30 is inserted into the incision. Sleeves 31 and 32 are then advanced distally to drive tines 12 of ring 10 into the tissue, so that the tines penetrate the tissue and engage the tine-forming surface 30A of anvil 30, and so that the tines begin to curl radially inward (toward the central axis of anvil 30) as they advance against anvil surface 30A. Then, as shown in FIG. 5, while sleeves 31 and 32 press ring 10's flat ring portion 11 in the distal direction against the vessel's exterior surface 40, anvil 30 is retracted in the proximal direction (toward the top of FIG. 5) to cause surface 30A to begin to bend the distal portion of each tine 12 toward the top of FIG. 5 relative to the rest of ring 10. Since the tines 12 extend through the tissue, the tines grab the tissue as they bend, and the bending of the tines causes the incised tissue edges to begin to evert. Then, as shown in FIG. 6, sleeve 31 is retracted in the proximal direction while anvil 30 continues to 10 retract in the proximal direction. In response to the force exerted on tines 12 by retracting anvil 30 (when sleeve 31 has retracted proximally), each tine 12 folds or buckles at its hinge (or weak portion) radially outward (away from the central axis of anvil 30) as it continues to grab the tissue, thereby completing the eversion of the incised tissue edges as shown in FIG. 6. After such folding or buckling of tines 12, sleeve 32 is withdrawn or retracted in the proximal direction, leaving ring 10 installed at the incision with tines 12 holding the incised tissue edges in the desired everted state (for joining to tissue of another vessel or other organ). Optionally, a final step is performed in which an another element (not shown in FIGS. 4–6) of the installation tool is advanced into engagement with ring 10 (or the tissue that has been grabbed thereby), or in which anvil 30 is again advanced into the incision and sleeves 31 and 32 are then advanced against anvil 30, to further bend the tines 12 relative to the rest of ring 10 and thereby further evert the incised tissue edges. The optional final step is included in preferred embodiments of the invention.

Figure 7:
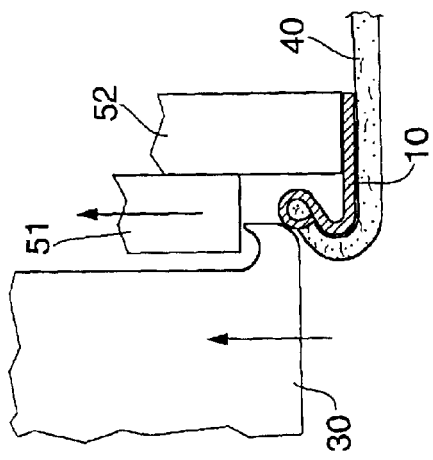
FIG. 7 is a side cross-sectional view of a portion of the ring of FIG. 1 and a portion of an alternative apparatus for installing it, at an early stage of installation of the ring around an incision in the sidewall of a blood vessel.
Figure 8:
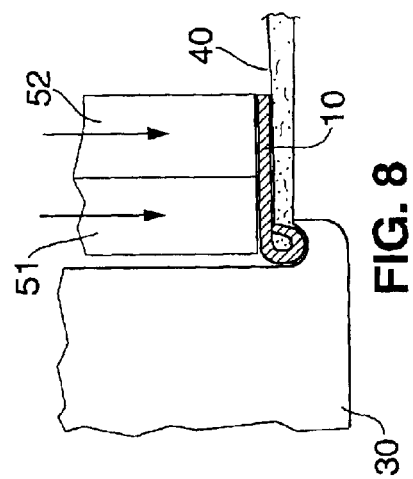
FIG. 8 is a side cross-sectional view of a portion of the ring of FIG. 1 and a portion of the FIG. 7 installation apparatus, at an intermediate stage of installation of the ring around an incision in the sidewall of a blood vessel.
Figure 9:
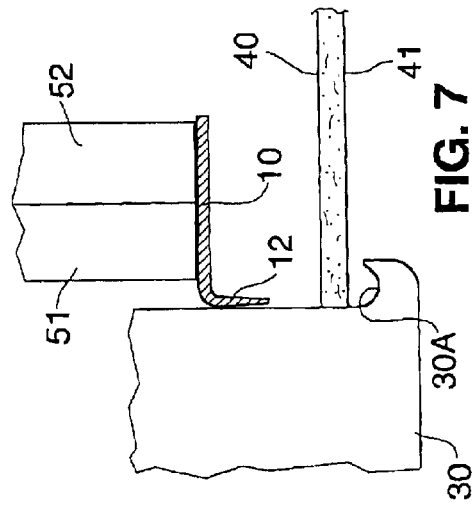
FIG. 9 is a side cross-sectional view of a portion of the ring of FIG. 1 and a portion of the FIG. 7 installation apparatus, at a late stage of installation of the ring around an incision in the sidewall of a blood vessel.

Preferably (and as an alternative to the procedure described with reference to FIGS. 4–6), ring 10 is installed using a slightly different installation tool that comprises anvil 30 and independently translatable sleeves 51 and 52 (as shown in FIGS. 7, 8, and 9) at the site of an incision in the side wall of a blood vessel having exterior surface 40 and interior surface ("intima") 41. Only the right half of the distal portion of each of elements 30, 51, and 52, and the right edge of the incision (whose axis of symmetry extends perpendicular to the plane of FIG. 7) are shown in FIGS. 7, 8, and 9. FIG. 7 shows ring 10 and the installation tool at an early stage of the installation process, FIG. 8 shows them at a later stage, and FIG. 9 shows them at a still later stage. When anvil 30 has retracted (upward) into the position shown in FIG. 9, ring 10 has been installed with ring portion 11 extending around the incision, tines 12 grabbing the tissue around the incision, and tines 12 having been deformed so as to evert the incised edges of the tissue to expose the intima 41 of the blood vessel as shown in FIG. 9.

More specifically, as shown in FIG. 7, anvil 30 is inserted into the incision. Then, sleeves 51 and 52 are advanced distally (relative to anvil 30) to drive tines 12 of ring 10 between anvil 30 and the incised tissue edges until the tips of tines 12 engage the tine-forming surface 30A of anvil 30, and begin to curl radially outward (away from the central axis of anvil 30) as they advance against anvil surface 30A. Sleeves 51 and 52 continue to advance until they reach the position shown in FIG. 8, in which they have pressed ring 10's flat ring portion 11 in the distal direction against the vessel's exterior surface 40, and caused the distal portion of each tine 12 to bend (against stationary surface 30A of anvil 30) relative to the rest of ring 10 until the tip of each tine has penetrated (and grabbed) the tissue around the incision. Then, as shown in FIG. 9, sleeve 51 and anvil 30 are retracted (in the proximal direction) while sleeve 52 remains extended in engagement with ring 10. In response to the force exerted on tines 12 (and the incised tissue edges that have been grabbed by tines 12) by retracting anvil 30, each tine 12 folds or buckles at its hinge (or weak portion) radially outward (away from the central axis of anvil 30) while continuing to grab the tissue, thereby everting the incised tissue edges as shown in FIG. 9. After such folding or buckling of tines 12, sleeve 52 is retracted in the proximal direction or otherwise withdrawn, leaving ring 10 installed at the incision with tines 12 holding the incised tissue edges in the desired everted state (so that the everted tissue can be joined to tissue of another vessel or other organ).

Optionally, a final step is performed in which an another element (not shown in FIGS. 7–9) of the installation tool is advanced into engagement with ring 10 (or the tissue that has been grabbed thereby), or in which anvil 30 is again advanced into the incision and sleeves 51 and 52 are then advanced against anvil 30, to further bend the tines 12 relative to the rest of ring 10 and thereby further evert the incised tissue edges.

FIGS. 10 and 13 are perspective views of anastomosis ring 60, which is an embodiment of the inventive anastomosis ring. Ring 60 includes ten malleable tines 61 which extend out from cylindrical (tubular) ring portion 65. FIG. 10 shows tines 61 in their initial configuration (the configuration in which they would be when ring 60 is loaded onto an installation tool prior to installation at an incision in an organ). FIG. 13 shows each of tines 61 in its final configuration (the configuration in which it would be following installation at an incision in an organ).

Each tine 61 of ring 60 has a flat cross-section, with two opposed faces and relatively small (narrow) edge surfaces between the faces. Each tine 61 has a relatively wide proximal end 64 (from which it extends out from ring portion 65) and tapers to a sharp distal end 62. Each tine 61 is preferably made from flat metal, and has a weak portion 63 which is defined by a hole formed (e.g., stamped or etched) therethrough (from one of the opposed faces to the other) at a location between ends 62 and 64. Prior to installation, each tine 61 is preformed into an S-shape as shown in FIG. 10, so that the tines' distal portions are oriented in a distal direction (so that the tines' distal portions are generally parallel to each other and to the axis of symmetry of ring 60). During the installation process, a distal portion of each tine is curled radially outward (away from ring 60's axis of symmetry) so that it grasps tissue, and then the curled tines are folded (or buckled) radially outward about their weak portions to evert the tissue being grasped thereby, until each tine 61 reaches the final configuration shown in FIG. 13. As shown in FIGS. 13 and 14, when tines 61 are in their final configuration, the folded portion 67 of each tine that is farthest from the ring's tubular portion 65 is at (or very near to) the tine's weak portion 63. Assuming that the central axis of tubular portion 65 is oriented vertically, the folded portion 67 is preferably slightly raised in the sense that it is slightly above the tine's lowest portion (66). When ring 60 has been installed around an incision in a vessel 68 (with tines 61 in the configuration shown in FIG. 14 so as to evert the incised tissue edges), and vessel 68 is to be joined (at an anastomosis site) to a second vessel 69 that has been prepared for anastomosis by installation of an anastomosis ring (similar or identical to ring 60) around an incision in the second vessel, the folded, raised portions 67 of tines 61 (of ring 60) desirably shape the everted, incised tissue edges of vessel 68. Specifically, the fact that portions 67 are raised (relative to portions 66) causes ring 60 to present the intima of vessel 68 to the intima of vessel 69 in an orientation that promotes healing together of, and formation of a fluid tight seal between, the joined tissue of vessels 68 and 69.

A variation on ring 60 will be described with reference to FIG. 15. This ring, identified by reference numeral 60', has a tubular central ring portion 65' and ten malleable tines 61' which extend out from the tubular ring portion.

FIG. 15 shows one of tines 61' in its initial configuration (the configuration in which it would be when ring 60' is loaded onto an installation tool prior to installation at an incision in an organ). The other tines 61' of ring 60' are omitted from FIG. 15 for clarity. Each tine 61' has a flat cross-section, with two opposed faces and relatively small (narrow) edge surfaces between the faces. Each tine 61' has a pair of notches 63' in the edge surfaces at a first distance from ring portion 65'. These notches define a weak portion of tine 61' at said first distance from ring portion 65'.

Ring 260 (shown in phantom view in FIGS. 11 and 12) differs from ring 60 (of FIGS. 10, 11, and 12) in the following respects. In ring 60's pre-installation configuration, each of its tines 61 (which extend out from ring 60's cylindrical portion 65) has a distal portion 61A that is oriented vertically (when ring 60 is viewed as in FIG. 11) and terminates at a sharp tip 62, a straight proximal portion 61B oriented at a forty-five degree angle relative to distal portion 61A, and a horizontally oriented straight portion 61C between portions 61A and 61B. Ring 260 (shown in phantom view in FIGS. 11 and 12) has a central cylindrical portion which is identical to cylindrical portion 65 of ring 60. However, each tine 261 of ring 260 in its pre-installation configuration extends out from ring 260's cylindrical portion with a distal portion that is oriented vertically (when ring 260 is viewed as in FIG. 11), a curved proximal portion R, and a horizontally oriented third portion between the distal portion and the curved proximal portion. An important difference between the curved tines 261 of ring 260 and the piecewise linear tines 61 of ring 60 is that, in the ring installation step to be described with reference to FIG. 22, tine 261 will bend and rotate farther than tine 61 due to the cam action of surface 76 of sleeve 75 on the smoothly curved tine 261. This additional bending and rotation of tines 261 (to move them from a configuration corresponding to that shown in FIG. 21 to a configuration corresponding to that shown in FIG. 22) allows sleeves 72, 73, and to more easily form the final bend in each tine 261 as sleeves 72, 73, and 74 advance to press tines 261 against surface 76 (during the installation step to be described with reference to FIG. 24).

Next, with reference to FIGS. 16–25, we describe a tool 79 for installing ring 80 (partially shown in each of FIGS. 16–25), in tissue around an opening in an organ (e.g., an incision in a blood vessel). With respect to all embodiments of tools for installing the inventive rings disclosed herein, it is contemplated that the multiple movements of the various sleeves can be automated and synchronized to some degree such that the installation process requires a minimal number of operator manipulations of the installation tool. Ring 80 can be identical to ring 60 of FIG. 14. In ring 80's pre-installation configuration, each of its tines 80A (which extend out from ring 80's cylindrical portion 85) has a distal portion 81 that is oriented vertically (when ring 80 is viewed as in FIG. 17) and terminates at a sharp tip 82, a proximal portion 83 oriented at a forty-five degree angle relative to distal portion 81, and a horizontally oriented third portion 84 between portions 81 and 83.

Each tine 80A of ring 80 will preferentially fold at the junction between angled portion 83 and portion 84 (e.g., in response to forces exerted on ring 80 by retracting anvil 70 during the installation step shown in FIG. 20, and forces exerted on ring 80 by anvil 70 and sleeves 74 and 75 during the installation step shown in FIG. 24). Each tine 80A preferably also has a weak portion (e.g., a hinge) at a location near to (but spaced from) the junction between portions 83 and 84, so that each tine 80A preferentially bends at both this junction and the weak portion during the steps described with reference to FIGS. 20 and 24. FIG. 25 is a simplified perspective view of the distal end of tool 79 with ring 80 (in its initial configuration) mounted thereon, showing some of tines 80A of ring 80. Each tine 80A has a hole 86 extending through it (at a location along tine portion 84), each hole 86 defining a weak portion of the tine.

FIG. 25A is a perspective view of ring 80 around a preferred (fluted) implementation of anvil 70. Anvil 70 of FIG. 25A has grooves along its sides, and concave, tine-forming portions 70B of its surface 70A. Each concave portion 70B is dimensioned and positioned to receive and form one of the tines of ring 80.

With reference to FIGS. 16–24 we next describe operation of installation tool 79 which comprises anvil 70 and independently translatable sleeves 71, 72, 73, 74, and 75, during installation of an anastomosis ring 80 in an organ (the organ is not shown). Only the right half of the distal portion of each of elements 71, 72, 73, 74, and 75, the distal portion of anvil 70, and the right half of ring 80, are shown in FIGS. 16–24. Tool 79 also comprises control assembly 79A (shown only in FIG. 16) which is coupled to anvil 70 and sleeve elements 71–75 and configured to independently advance and retract appropriate ones of elements 70–75 at appropriate times. It is contemplated that some implementations of assembly 79A are manually operated in the sense that a user must manually manipulate at least one element of 79A to accomplish each advancing or retracting movement of each desired one of elements 70–75, and that other implementations of assembly 79A are automatically operated in the sense that they include a trigger, and hardware for implementing a timed sequence of advancing and retracting movements of elements 70–75 in response to a single actuation of the trigger. Other embodiments of the inventive installation tool (including those described with reference to FIGS. 4–9 and 41–57) have control assemblies coupled to the tool's anvil and sleeve elements and configured to advance and retract appropriate ones of the anvil and sleeve elements at appropriate times.

Initially, ring 80 is loaded onto tool 79 with tubular portion 85 in circular slot 74A of sleeve 74 (shown in FIGS. 16 and 17), and tines 80A of ring 80 held between sleeves 71, 72, 73, 74, and end portion 76 of sleeve 75 as shown in FIG. 16. Then, anvil 70 is inserted into the incision (or other opening) in the organ, and sleeves 71, 72, 73, 74, and 75 are then advanced (distally) together as a unit to drive tines 80A between anvil 70 and the tissue edges until the tips of tines 80A engage the tine-forming surface 70A of anvil 70, and begin to curl radially outward (away from the central axis of anvil 70) as they advance against anvil surface 70A. Sleeves 71, 72, 73, 74, and 75 continue to advance until they reach the position shown in FIG. 17, in which they have pressed portion 84 of each tine 80A against the organ's exterior surface and caused distal portion 81 of each tine 80A to bend (against stationary surface 70A of anvil 70) relative to the rest of ring 80 until the tip 82 of each tine has penetrated (and grabbed) the tissue around the opening. The distal end of sleeve 73 is angled to match the slope of each of tine portions 83 of ring 80 in its FIG. 16 configuration. FIG. 16 shows one tine 80A whose tip has been advanced into engagement with surface 70A (but which has not yet begun to curl), and FIG. 17 shows the same tine after it has been advanced further (by sleeves 71, 72, 73, 74, and 75) and begun to curl radially outward.

Then, while sleeves 71–75 remain stationary, anvil 70 is retracted (toward the top of FIG. 18) to further curl the curled distal portion 81 of each tine 80A relative to the rest of ring 80 into the configuration shown in FIG. 18, thereby causing portion 81 of each tine to further penetrate and more securely grab the tissue around the opening.

Then, as shown in FIG. 19, sleeves 71 and 72 are retracted in the proximal direction (toward the top of FIG. 19) while sleeves 73, 74, and 75 and anvil 70 remain stationary in engagement with ring 80.

Then, as shown in FIG. 20, anvil 70 is retracted (in the proximal direction) relative to sleeves 73, 74, and 75. In response to the force exerted by anvil 70 on tines 80A (and the tissue edges that have been grabbed by tines 80A), each tine 80A folds or buckles at both its weak portion and at the junction (identified by reference numeral 83A in FIGS. 17 and 25) between portions 83 and 84, so that its curled distal portion 81 moves radially outward (away from the central axis of anvil 70) while it continues to grab the tissue, thereby everting the tissue edges. As noted, each tine 80A preferably has a weak portion (e.g., a hinge) at a location spaced from the junction (83A) between portions 83 and 84. In one implementation, this weak portion is determined by a hole 86 (shown in and described above with reference to FIG. 25) in each tine. Each hole 86 is preferably located along the tine such that, when tines 80A are in their final configuration (shown in FIG. 24), the portion (87) of each tine that is farthest (radially) from the ring's tubular portion 85 does not coincide with the junction 83A, and such portion 87 coincides with (or is very near to) hole 86. In this preferred implementation, hole 86 extends through portion 84 of each tine 80A at a location near to, but spaced from junction 83A between portions 83 and 84. Such separation between hole 86 and junction 83A (and greater distance between portion 85 and hole 86 than between portion 85 and junction 83A) is preferred because it reduces trauma to tissue in the following sense during installation of ring 80 in the tissue. When ring 80 has been installed in the tissue in its final configuration (shown in FIG. 24), the installation procedure has not stretched the tissue along portion 83 of each tine (which is not shown in FIG. 24, but which would be between portion 83 and sleeve portion 76). In contrast, the tissue in immediate contact with tip 82 of each tine has undergone significant stretching. The degree of stretching which the tissue has undergone is roughly proportional to the tissue's distance (along each tine from tip 82 to portion 87) from tip 82, with tissue nearer to portion 87 (along the tine's axis) having undergone less stretching than tissue farther from portion 87 along the tine's axis. Thus, since the preferred location of the tine's weak portion effectively moves portion 87 closer (along the tine's axis) to tip 82 than it would be if the weak portion were not present (or if the weak portion had coincided with junction 83A), the weak portion effectively reduces the amount of stretching undergone by the tissue during ring installation.

Each tine 80A preferentially bends at both junction 83A and at the weak portion (the location of hole 86) during the steps described with reference to FIGS. 20 and 24.

After the folding or buckling of tines 80A described with reference to FIG. 20, sleeve 73 is retracted in the proximal direction (as shown in FIG. 21), leaving ring 80 (and the tissue gripped thereby) between anvil 70 and sleeves 71, 72, 74, and 75, with sleeve 74 in a retracted position relative to sleeve 75.

Then, sleeve 74 is advanced distally relative to sleeve 75 (into the position shown in FIG. 22) to bend and rotate each tine 80A (relative to the rest of ring 80) from the configuration shown in FIG. 21 to that shown in FIG. 22 as a result of force exertion on ring 80 by stationary sleeve 75 and the distal end of advancing sleeve 74. This bending and rotation further everts the tissue edges around the organ opening, causes the tines 80A to penetrate farther into the tissue, and allows sleeves 72, 73, and 74 to more easily form a final bend in each tine 80A (in the step to be described with reference to FIG. 24). When ring 80 has been formed into the configuration shown in FIG. 22, portion 85 is at least substantially perpendicular to portion 83 of each tine 80A, and portions 83 and 85 are supported by sleeve 75.

After ring 80 has been placed in the configuration shown in FIG. 22, sleeve 74 is retracted in the proximal direction relative to portion 76 of sleeve 75, into the position shown in FIG. 23.

Then, sleeves 72, 73, and 74 are advanced distally relative to portion 76 of sleeve 75 to press tines 80A and portion 85 against portion 76, thereby forming a final bend in each of tines 80A relative to portion 85 and moving the ring 80 into the final, installed configuration shown in FIG. 24. Specifically, portions 81, 82, and 84 of each tine 80A are bent radially outward relative to portion 83 and then pushed distally against portion 83 to put ring 80 in the final configuration. In this final configuration, ring 80 is installed at the opening in the organ with tines 80A holding the tissue edges in the desired everted state (so that the everted tissue can be joined to tissue of another vessel or other organ).

After installation of ring 80, sleeve 75 is (e.g., portions comprising the distal end of sleeve 75 are) spread or dilated (radially outward away from anvil 70's central axis of symmetry) to decouple tool 79 from the installed ring, and tool 79 is removed from the installed ring.

In tool 79 (described with reference to FIGS. 16–24), flat portion 84 of each tine 80A conforms with the flat upper surface of portion 76 of sleeve 75 during the step described with reference to FIG. 23, so that sleeves 72, 73, and 74 can efficiently form the final bend in each tine 80A as sleeves 72, 73, and 74 advance to press tines 80A against surface 76 (during the step described with reference to FIG. 24). Variations on installation tool 79 (e.g., those used to install rings having curved tines, such as ring 60) can include a sleeve that corresponds functionally to sleeve 75 but has a tine-receiving surface (corresponding to the upper, tine-receiving surface of portion 76) that is not flat, but is instead curved to match the curvature of tines of rings to be installed by such tool.

In variations on the described embodiments of the inventive tined anastomosis ring, the weak point of each tine is determined other than by a hole through the tine. For example, the weak point can be determined by notches cut into the tine (to reduce the tine's width), a tine portion having reduced thickness, or perforations cut into the tine.

In variations on the described embodiments of the inventive tined ring, the ring portion (from which the tines, and optionally also docking features, protrude) is not malleable. For example, the ring portion can be rigid or elastic. The ring portion is preferably integrally formed from metal, but can alternatively have another structure. For example, the ring portion can be assembled from component parts (e.g., metal parts) which are connected together (e.g., by welding), or can be made (entirely or partially) of material other than metal but which has the required mechanical properties (e.g., flexibility and/or moldability).

Next, with reference to FIGS. 26–28, we describe installation tool 90 which is another embodiment of the inventive tool for installing ring 80 (or variations on this embodiment of the inventive tined ring) around an opening of an organ (e.g., an incision in a blood vessel). Installation tool 90 includes anvil 70 and independently translatable sleeves 71, 72, 73, and 74 which are identical to the corresponding, identically numbered, elements of tool 79 described above with reference to FIGS. 16–25. Tool 90 also includes sleeve 95 and annular disk 96 (which together replace sleeve 75 of above-described tool 79), and hardware (not shown) for advancing and retracting elements 70, 71, 72, 73, 74, and 95 at desired times. The inner radius of annular disk 96 is equal to the inner radius of portion 76 of sleeve 75 of tool 79, and the width of disk 96 (from its inner to outer radius) is such that the overall distance from the inner radius of disk 96 to the outer radius of the distal portion of sleeve 95 is equal to the overall distance from the inner radius of portion 76 of sleeve 75 to the outer radius of sleeve 75's distal portion.

Tool 90 can be used to install ring 80 at the site of an incision in the side wall of a blood vessel (shown in FIG. 28 but not FIG. 26) having exterior surface 40 and interior surface (inside lining or "intima") 41. FIG. 26 is a cross-sectional view of the right half only of the distal portion of each of elements 71, 72, 73, 74, and 95, and the right half of ring 80 and disk 96. Disk 96 is oblong (with an open center) or annular.

FIG. 26 shows ring 80 and tool 90 at an early stage of the installation process. To load ring 80 and disk 96 at tool 90's distal end, ring portion 85 is inserted into slot (or groove) 74A of sleeve 74, and disk 96 is inserted in groove 95A in sleeve 95's inner sidewall. Each of slot 74A and groove 95A is circular or oblong (e.g., each is circular when the tubular central portion of ring 80 is circular and disk 96 is annular). Sleeve 95 (or the distal end of sleeve 95) can comprise multiple portions which can be moved radially toward each other (to grip the disk 96) or radially away from each other (to release the disk 96). The portions comprising sleeve 95's distal end are spread or dilated radially outward (away from each other and away from the central axis of symmetry of anvil 70) to allow insertion of disk 96 in (or removal of disk 96 from) groove 95A, or contracted radially inward (toward the central axis of anvil 70) so that disk 96 is gripped between sleeve 95 and tines 80A of ring 80. In alternative embodiments of the invention, sleeve 95 includes an element which releasably holds disk 96 in groove 95A. In other alternative embodiments, disk 96 (or a variation thereon) is removably mounted to a sleeve (sleeve 95 or a variation thereon) by a joining feature other than a groove or notch in the sleeve.

When ring 80 and disk 96 have been loaded onto the distal end of tool 90, tool 90 is operated to install ring 80 at an incision or other opening in an organ. To accomplish this, tool 90 operates in essentially the same manner as above-described tool 79 would operate to install the same ring, with elements 95 and 96 of tool 90 together corresponding functionally to sleeve 75 of tool 79, except in that disk 96 remains at the anastomosis site (with the fully installed ring) after sleeve 95 and the other elements of installation tool 90 are removed from the anastomosis site.

For the following reason, tool 90 can have a simpler design than that of tool 79, and removal and release of tool 90 following installation of a ring can be easier than removal and release of tool 79 following ring installation. The radial distance over which the distal end of sleeve 95 must move (distance "A" in FIG. 27) to release disk 96 and to release portion 85 of ring 80 from between sleeves 74 and 95 is much less than the radial distance over which the distal end of sleeve 95 would need to move (distance "B" in FIG. 27) to release portion 85 from elements 74, 95, and 96 if disk 96 were integrally formed with (or permanently attached to) sleeve 95, assuming that the overall distance from the inner radius of disk 96 to the outer radius of sleeve 95 is equal to the overall distance from the inner radius of portion 76 of sleeve 75 to the outer radius of the distal end of sleeve 75.

Also, sleeve 95 of tool 90 (and sleeve 75 of tool 79) are typically made of plastic, but it is practical to implement disk 96 as a metal disk. A metal implementation of disk 96 would typically be stronger than a typical plastic implementation of portion 76 of sleeve 75.

When tool 90 has completed the installation of ring 80 at an incision in a blood vessel (as shown in FIG. 28), ring portion 85 extends around the incision, tines 80A have grabbed the tissue around the incision and then been deformed so as to evert the incised edges of the tissue to expose the intima 41 of the blood vessel, and disk 96 is trapped between the vessel's exterior surface 40 and tines 80A. Ring 80 can be implemented with docking features (and optionally also fasteners) that extend out from ring portion 85. Alternatively, disk 96 can be implemented with docking features (and optionally also fasteners) that extend out from disk 96's outer periphery (for use in aligning ring 80 with, and optionally also attaching ring 80 to, another anastomosis ring). In the latter case, ring 80 is preferably implemented without docking features or fasteners to simplify its design.

When only the inventive tined anastomosis ring (and not also an additional element such as annular disk 96 of FIG. 28) is to be installed, the ring is preferably implemented to have one or more fasteners extending out from its central ring portion (the ring portion from which its tines extend). Preferred implementations of such fasteners will next be described with reference to FIGS. 29–40. Each fastener will be described as a feature of an embodiment of a tined anastomosis ring having a tubular central ring portion, although each fastener can be implemented as a feature of an anastomosis ring having a flat central ring portion, or as a feature of an annular ring (e.g., ring 96 of FIG. 28) to be installed with any embodiment of the inventive tined anastomosis ring.

FIG. 29 is a perspective view of portions of two of the inventive anastomosis rings (ring 100 and ring 110) which have been aligned together, and respectively include fasteners 101 and 111 which are tabs. Each of rings 100 and 110 has a tubular central portion (having the same shape as portion 65 of ring 60 of FIG. 10), with tines (not shown) that extend out from such tubular central portion. Ring 100 has tabs 101 that extend up from its tubular central portion at locations evenly spaced around the tubular central portion. Only one tab 101 is shown in FIG. 29. Each tab 101 has notches 102 at the junction between tab 101 and ring 100's tubular central portion.

Ring 110 has one slotted tab 111 for each tab 101 of ring 100. Each tab 111 has a proximal portion 112 at the junction between tab 111 and ring 110's tubular central portion, and a distal end defining a slot 113. Each tab 111 is bent into the shape shown in FIG. 29, so that tab 101 of ring 100 can be advanced upward through slot 113 to align the rings 100 and 110 together. When rings 100 and 110 have been aligned as shown, they are fastened together by bending each tab 101 radially outward and downward relative to table 111 so that tab 100 folds into an orientation that locks ring101 together with ring 100. The notches 102 in each tab 101 define a weak point at which tab 101 preferentially folds when it is bent as described.

Tab 121 (of anastomosis ring 120) of FIG. 30 is a variation on tab 101 of FIG. 29. Anastomosis ring 120 has tabs 121 which extend up from its tubular central portion at locations evenly spaced around the tubular central portion, and tines (not shown) that extend down from its tubular central portion. Only one tab 121 is shown in FIG. 30. Tab 121 differs from tab 101 only in that its weak portion (at the junction between tab 121 and ring 120's tubular central portion) is defined by a slot 122 extending through tab 121, rather than by notches (e.g., notches 102 of FIG. 29) in the tab's sides.

Tab 131 (of anastomosis ring 130) of FIG. 31 is another variation on tab 101 of FIG. 29. Anastomosis ring 130 has tabs 131 which extend up from its tubular central portion at locations evenly spaced around the tubular central portion, and tines (not shown) that extend down from its tubular central portion. Only one tab 131 is shown in FIG. 31. Tab 131 differs from tab 101 in that its weak portion 131A (which can be a thin portion of tab 131) is oriented vertically, and in that it has a notch 132 at the junction between tab 131 and ring 130's tubular central portion. To fasten ring 130 to ring 110, each tab 131 is bent or folded at its weak portion 131A. In contrast, the weak portion of tab 101 is defined by a set of notches (e.g., notches 102 of FIG. 29) in the tab's sides.

FIGS. 32 and 33 are perspective views of portions of two aligned anastomosis rings (rings 140 and 150) having a different type of tab fasteners for fastening the rings together. Ring 140 has tabs 141 which extend out from around its tubular central portion, and ring 150 has tabs 151 which extend out from around its tubular central portion. Only one tab 141 and one tab 151 are shown in each of FIGS. 32 and 33. When rings 140 and 150 are aligned, each tab 141 has a flange 142 that circumferentially overlaps an edge 152 of one of tabs 151. Tabs 141 and preferably also tabs 151 are made of spring metal (or are otherwise biased to remain in their originally manufactured orientations relative to the rest of the ring from which they protrude). To fasten ring 140 to ring 150, each tab 141 is bent below the adjacent tab 151 (assuming that the rings are oriented with tabs 141 initially above tabs 151), with flange 142 bending relative to the rest of tab 141 to allow it to pass edge 152 of tab 151. After such relative movement, tabs 141 and 151 have the relative positions shown in FIG. 33, with spring force exerted by each tab 141 on tab 151 holding the rings together and tabs 151 preventing tabs 141 from springing back into their original position (i.e., the original position shown in FIG. 32).

Next, with reference to FIGS. 34 and 35, we describe another type of fastener which can be included as part of the inventive anastomosis ring. FIG. 34 is a side cross-sectional view of portions of two aligned anastomosis rings (rings 160 and 180) having spring fasteners for fastening the rings together. Each spring fastener comprises elements 163 and 181. Fastener elements 163 are made of spring metal, are generally U-shaped, and each has a body which extends out at an acute angle from an edge (the bottom edge in FIG. 34) of ring 160's tubular central portion, with the body of each element 163 being attached at a proximal end portion 162 to the tubular central portion of ring 160. Each element 163 has two tabs 161, which extend out at an obtuse angle with respect to the body of element 163 (as shown in FIG. 34). When element 163 (in its FIG. 34 configuration) is rotated (counterclockwise in FIG. 34) about end portion 162 relative to ring 160's tubular central portion, element 163 will spring back to the configuration shown in FIG. 34. Each fastener element 181 is made from malleable material, and has two wings 182. Each wing 182 is pre-formed to extend in a plane oriented at a ninety-degree angle relative to the rest of the element 181 of which it is a part. When ring 180 is oriented with a vertical axis of symmetry, each element 181 extends vertically (or substantially vertically) upward away from ring 180's tubular central portion (as shown in FIG. 34).

To fasten ring 160 to ring 180, a surgeon (or a surgeon-operated instrument) aligns ring 180 with ring 160 by positioning the tubular central portion of ring 180 (which has a slightly larger diameter than does the tubular central portion of ring 160) around the tubular central portion of ring 160 so that the rings have a common axis of symmetry (which we shall refer to as being "vertical" to simplify the description) and so that an element 181 of ring 180 extends between the tabs 161 of each element 163 of ring 160 (in the relative orientation shown in FIG. 35). In some implementations of the rings, as the rings are aligned, tabs 161 of one element 163 (on one side of ring 160's tubular central portion) are temporarily displaced toward the tabs 161 of another element 163 (on another side, typically the opposite side, of ring 160's tubular central portion), thus bending each of the elements 163 about its end portion 162 toward the ring 160's tubular central portion, and then the opposed tabs 161 spring back (relax) away from each until each element 163 exerts spring force radially outward against the tubular central portion of ring 180. In other implementations of the rings, elements 163 are not elastic. After the rings are aligned, wings 182 of each element 181 are spread apart by folding each wing 182 (outward in the directions of arrows A in FIG. 35, about a vertical axis) over an adjacent one of horizontally oriented tabs 161. When this has been accomplished, the forces between fastener element 163 (including tabs 161) and wings 182 fasten together the aligned rings 160 and 180. In the final configuration, the tabs 161 on both sides of element 181 provide circumferential support to prevent rotation of ring 160 relative to ring 180 about their common axis.

A variation on fastener element 181 of FIG. 35 will next be described with reference to FIG. 36. The fastener elements of FIG. 36 implement an embodiment of the inventive tined anastomosis ring fastener. In FIG. 36, ring 160 is identical to ring 160 of FIGS. 34 and 35, but ring 170 differs from ring 180 (of FIGS. 34 and 35) in that it has fastener elements 171 which are shaped differently than fastener elements 181 of FIG. 35. Each fastener element 171 has a spring portion 173, and a body 172 which ends at free edge 174. When ring 170 is oriented with a vertical axis of symmetry, the spring portion 173 of each element 171 extends at least substantially vertically upward away from the upper edge of ring 170's tubular central portion (as shown in FIG. 36). At least the spring portion 173 of each element 171 is made of spring metal (or portion 173 is otherwise biased so that element 171 tends to remain in its originally manufactured orientation). To fasten ring 160 to ring 170, a surgeon (or a surgeon-operated instrument) aligns ring 170 coaxially with ring 160 by positioning the tubular central portion of ring 170 (which has diameter slightly larger than does the tubular central portion of ring 160) around the tubular central portion of ring 160 so that the rings have a common axis of symmetry (which we shall refer to as being "vertical" to simplify the description) and so that an element 171 of ring 170 extends between the tabs 161 of each element 163 of ring 160 (in the relative orientation shown in FIG. 36). Then, as ring 170 is moved vertically upward into horizontal alignment with ring 160, the central sloping portion of body 172 (between wings 176 of body 172) slides over element 163 and/or the tubular central portion of ring 160, while spring portion 173 is displaced radially outward relative to ring 170's tubular central portion to allow the thickest portion of element 171 to pass over ring 160's tubular central portion. In some implementations of the rings, when the rings are aligned, tabs 161 of one element 163 (on one side of ring 160's tubular central portion) are temporarily displaced toward tabs 161 of another element 163 (on another side, typically the opposite side, of ring 160's tubular central portion), thus bending each of the elements 163 about its end portion 162 toward the ring 160's tubular central portion, and then the opposed tabs 161 spring back (relax) away from each other until each element 163 exerts spring force radially outward against the tubular central portion of ring 170. In other implementations of the rings, elements 163 are not elastic. When edge 174 has moved vertically above the upper edge of ring 160's tubular central portion, spring portion 173 springs back (radially inward) into its at least substantially vertical orientation (as shown in FIG. 36). When this has been accomplished, the forces between edge 174 and ring 160's tubular central portion and between fastener element 163 (including tabs 161) and ring 170 fasten together the aligned rings 160 and 170.

Variations on the FIG. 36 embodiment employ fastener elements which are differently shaped than elements 163 and 173 of FIG. 36. For example, FIG. 37 is a perspective view of a portion of tined anastomosis rings 170' and 160', each embodying the invention. Ring 170' has a tubular central portion and a number of spring fastener elements 171'. Each element 171' is made of spring metal (or is otherwise biased to remain in its originally manufactured orientation relative to the rest of ring 170') and has a shape which is a variation on that of above-described spring fastener element 171. Preferably, elements 171' are integrally formed with the rest of ring 170'. Each fastener element 171' has a spring portion 173' (which corresponds functionally to spring portion 173 of element 171), and a body having two tabs 174'. Ring 160' (of FIG. 37) is identical to ring 160 (of FIG. 36) except in that its fastener elements 163' have straight circumferential support tabs 161' that are oriented vertically; not bent circumferential support tabs with vertical portions and horizontally extending ends (e.g., bent circumferential support tabs 161 of ring 160). When ring 170' has been aligned with ring 160', elements 163' and elements 171' spring into a locked configuration in which they fasten together the aligned rings 160' and 170'. When rings 160' and 170' are aligned and fastened together, tabs 174' of each element 171' are between the tabs 161' of the corresponding one of elements 163', with the bottom surfaces of tabs 174' exerting downward force on the upper edge of the portion of element 163' between tabs 161' and on the upper edge of the tubular central portion of ring 170'.

Another type of fastener that can be used to hold together a pair of aligned anastomosis rings will be described with reference to FIG. 38. FIG. 38 is a perspective view of portions of two aligned anastomosis rings (rings 190 and 200). Each of rings 190 and 200 is a tined ring having a tubular central portion and fastener elements for fastening the rings together. The fastener elements of ring 190 are tabs 191 which extend out from ring 190's tubular central portion. Each tab 191 has a proximal end portion 192 at ring 190's tubular central portion and a distal end portion 193 that extends radially outside of ring 190's tubular central portion as shown in FIG. 38. The fastener elements of ring 200 are tabs 201 which extend radially outward from ring 200's tubular central portion. Each tab 201 has two parallel wings 202 which extend vertically from tab 201's central portion (when tab 201's central portion is oriented in a horizontal plane), and each wing 202 has a malleable end portion 203 as shown in FIG. 38.

To fasten ring 190 to ring 200, a surgeon (or a surgeon-operated instrument) lowers ring 190 into alignment with ring 200 by positioning the tubular central portion of ring 190 (which has a slightly smaller diameter than does the tubular central portion of ring 200) within the tubular central portion of ring 200 so that the rings have a common axis of symmetry and each tab 191 fits between the wings 202 of a different one of tabs 201. When the rings have been so aligned with each other, each fastener is moved into its locking configuration (to fasten together the aligned rings 190 and 200) by bending together the end portions 203 of wings 202 so that each tab 191 is held between a pair of bent-together end portions 203 and the rest of tab 201.

Another type of fastener that can be used to hold together a pair of aligned anastomosis rings will be described with reference to FIGS. 39 and 40. The embodiments of FIGS. 39 and 40 are variations on the snap fit fastener embodiment of FIG. 36. In each of FIGS. 39 and 40, ring 210 is a tined anastomosis ring having a tubular central portion and fastener elements for fastening ring 210 together with ring 190. Ring 190 (of FIGS. 39 and 40) is identical to ring 190 of FIG. 38, except in that tabs 191 of FIGS. 39 and 40 have their distal portions 193 extending vertically upward (rather than radially outward as in FIG. 38) prior to locking of ring 190 to another ring (i.e., ring 210), and tabs 191 of FIGS. 39 and 40 are malleable while tabs 191 of FIG. 38 can but need not be malleable. Note that the folded-over geometry of each tab 191 (with a proximal end portion 192 extending in a first vertical direction away from a first one of the top or bottom edge of ring 190's tubular central portion to a folded portion, and extending in the opposite vertical direction beyond the fold) is needed where there is no room to add features to other one of the top or bottom edge of the tubular central portion (such as where the ring's tines extend out from said other one of the top or bottom edge of the tubular central portion). The fastener elements of ring 210 are slotted tabs 211 which extend generally vertically upward from the upper edge of ring 210's tubular central portion as shown in FIG. 39. Each tab 211 has a slot 212 extending therethrough. One edge 213 of each slot 212 is formed so that it extends radially inward (relative to the opposite edge of slot 212) such that slot 212 is shaped to receive the distal end 193 of tab 191 when tab 191 is advanced vertically upward to bring ring 190 into alignment with ring 210 (as shown in FIG. 39). Tabs 191 and 211 (of the embodiment of FIGS. 39 and 40) are malleable. It is desirable to design tabs 211 to have the minimum possible vertical length, since if they are too long they may get in the way of one of the blood vessels joined at the anastomosis site. It is typically preferable to use fastener elements of the type to be described with reference to FIGS. 58–61 (rather than those of FIG. 39) since the fasteners of FIGS. 58–61 have lower vertical profile (than do those of FIG. 39) after two aligned rings are fastened together by folding the tabs 383, and since the FIG. 39 fasteners may provide less circumferential positioning support (especially where the rings' central portions are circular rather than oblong) than do the fasteners of FIGS. 58–61.

To fasten ring 190 to ring 210, a surgeon (or a surgeon-operated instrument) raises ring 190 into alignment with ring 210 by positioning the tubular central portion of ring 190 (which has a slightly smaller diameter than does the tubular central portion of ring 210) within the tubular central portion of ring 210 so that the rings have a common axis of symmetry and each tab 191 fits into slot 212 of a different one of tabs 211 as shown in FIG. 39. When the rings have been so aligned with each other, each fastener is moved into its locking configuration (to fasten together the aligned rings 190 and 210) by bending each pair of aligned tabs 211 and 191 radially outward (into the position shown in FIG. 40).

Next, an alternative embodiment of a tool for installing the anastomosis ring of the invention will be described with reference to FIGS. 41–48.

Installation tool 230 of FIGS. 41–48 comprises anvil 70 (which is identical to anvil 70 of FIGS. 16–24) and independently translatable sleeves 231, 232, 233, 234, and 235 (whose distal surfaces are shaped slightly differently than sleeves 71, 72, 73, 74, and 75 of FIGS. 16–24, as shown). FIGS. 41–48 show the configuration of tool 230 during each of eight different steps of installing tined anastomosis ring 220 in an organ (the organ is not shown). Ring 220 is identical to ring 80 of FIGS. 16–24, except in that its tines are longer relative to the height of its tubular central portion 221 than are the tines of ring 80 relative to the height of tubular central portion 85 of ring 80. Only the right half of the distal portion of each of elements 231, 232, 233, 234, and 235, and the right half of ring 220 are shown in FIGS. 41–48.

To install ring 220, the ring 220 is initially loaded onto tool 230 with tubular portion 221 in slot 234A of sleeve 234 (as shown in FIG. 41), and the tines of ring 220 held between sleeves 231, 232, and 234, and the end portion 236 of sleeve 235 (as shown in FIG. 41). Then, anvil 70 is inserted into the incision (or other opening) in the organ. Sleeve 234 of tool 230 differs from sleeve 74 of tool 79 in that sleeve 234 has two concentric slots 234A and 234B, each of which is circular or oblong, for receiving a tubular central portion (of a tined anastomosis ring) having a different diameter (largest radial dimension). Sleeve 74 has only one slot 74A. Thus, an anastomosis ring whose tubular central portion has a larger diameter than that of ring 220 can be loaded onto and installed by tool 230.

After ring 220 has been loaded and anvil 70 has been inserted into the opening in the organ, sleeves 231, 232, 233, 234, and 235 are advanced distally together as a unit to drive the tines of ring 220 between anvil 70 and the tissue edges, until the tines' tips engage the tine-forming surface 70A of anvil 70 and begin to curl radially outward (away from the central axis of anvil 70) as they advance against anvil surface 70A. Sleeves 231, 232, 233, 234, and 235 continue to advance until they reach the position shown in FIG. 42, in which they have pressed a horizontal portion of each tine (assuming that ring 220 is oriented with a vertical axis of symmetry as shown in FIG. 42) against the organ's exterior surface and caused the distal portion of each tine to bend (against stationary surface 70A of anvil 70) relative to the rest of ring 220 until the tip of each tine has penetrated (and grabbed) the tissue around the opening. The distal end of sleeve 233 is angled to match the slope of the angled proximal portion of each tine (of ring 220 in its FIG. 41 configuration). FIG. 42 shows one tine in the position it would have after its tip has penetrated the tissue and its distal portion has curled radially outward to grab the tissue.

Then, as shown in FIG. 43, sleeves 231 and 232 are retracted in the proximal direction (toward the top of FIG. 43) while sleeves 233, 234, and 235 and anvil 70 remain stationary in engagement with ring 220.

Then, as shown in FIG. 44, anvil 70 is retracted (in the proximal direction) relative to sleeves 233, 234, and 235. In response to the force exerted by anvil 70 on the tines of ring 220 (and the tissue edges that have been grabbed by the tines), each tine folds or buckles at both its weak portion (at location 223 shown in FIG. 44) and at the junction (identified by reference numeral 222 in FIGS. 43 and 44) between its horizontal and angled portions, so that its curled distal portion 224 moves radially outward (away from the central axis of anvil 70) while it continues to grab the tissue, thereby everting the tissue edges. Each tine preferably has a weak portion (e.g., a hinge) at a location spaced from the junction (222) between the tine's horizontal and angled portions. In one implementation, this weak portion is determined by a hole in each tine. Each hole is preferably located along the tine such that, when the tines are in their final configuration (shown in FIG. 48), the portion of each tine that is farthest (radially) from the ring's tubular portion 221 does not coincide with the junction 222, and such portion coincides with (or is very near to) the hole.

Each tine preferentially bends at both junction 222 and at its weak portion during the steps described with reference to FIGS. 44, 47, and 48.

After the folding or buckling of the tines described with reference to FIG. 44, sleeve 233 is retracted in the proximal direction (as shown in FIG. 45), leaving ring 220 (and the tissue gripped thereby) between anvil 70 and sleeves 234 and 235, with sleeve 234 in a retracted position relative to sleeve 235.

Then, sleeve 234 is advanced distally relative to sleeve 235 (into the position shown in FIG. 46) to bend and rotate each tine (relative the rest of ring 220) from the configuration shown in FIG. 45 to that shown in FIG. 46 as a result of force exertion on ring 220 by stationary sleeve 235 and the distal end of advancing sleeve 234. This bending and rotation further everts the tissue edges around the organ opening, causes the tines to penetrate farther into the tissue, and allows sleeves 232 and 233 to more easily form a final bend in each tine (in the step to be described with reference to FIGS. 47 and 48).

After ring 220 has been placed in the configuration shown in FIG. 46, sleeves 232 and 233 are advanced distally relative to portion 236 of sleeve 235 (as shown in FIG. 47) to press the tines against portion 236 (while sleeve 234 holds tubular portion 221 against portion 236), thereby further bending the tines relative to tubular portion 221. Sleeve 233 then continues to advance until a final bend has been formed in each tine relative to portion 221, and the ring 220 has been bent into the final, installed configuration shown in FIG. 48. Specifically, the curled distal portion of each tine is bent radially outward relative to the proximal portion of each tine (by sleeves 232 and 233, as shown in FIG. 47) and then pushed (by sleeve 233, as shown in FIG. 48) distally against the proximal portion to put ring 220 in the final configuration. In this final configuration, ring 220 is installed at the opening in the organ with its tines holding the tissue edges in the desired everted state (so that the everted tissue can be joined to tissue of another vessel or other organ).

After installation of ring 220, sleeve 235 is (e.g., portions comprising the distal end of sleeve 235 are) spread or dilated (radially outward away from anvil 70's central axis of symmetry) to decouple tool 230 from the installed ring, and tool 230 is removed from the installed ring.

Another alternative embodiment of a tool for installing one of the inventive anastomosis rings will next be described with reference to FIGS. 49–57.

Installation tool 330 of FIGS. 49–57 comprises anvil 70 (which is identical to anvil 70 of FIGS. 16–24) and four independently translatable sleeves 331, 332, 333, and 334 (which are shaped slightly differently than the five sleeves 231, 232, 233, 234, and 235 of FIGS. 41–48, as shown). FIGS. 49–57 illustrate the configuration of tool 330 during each of nine different steps of installing tined anastomosis ring 320 in incision 341 of blood vessel 340. Tool 330 of FIGS. 49–57 is a preferred embodiment of the inventive anastomosis ring installation tool, and it implements (during operation) a preferred embodiment of the inventive method for installing an anastomosis ring in an incision in a blood vessel (or another orifice of another type of organ).

Ring 320 is similar to ring 80 of FIGS. 16–24, but its tines (each comprising a distal portion 323 and a proximal portion 322) are formed so that when ring 320 is loaded onto tool 330 with its tubular central portion 321 oriented with a vertical axis of symmetry, proximal portions 322 are horizontal and distal portions 323 are vertical. Only the right half of the distal portion of each of elements 331, 332, 333, and 334, and the right half of ring 320 are shown in FIGS. 49–57.

To install ring 320, the ring 320 is first loaded onto tool 330 with tubular portion 321 in slot 333B of sleeve 333 (as shown in FIG. 49), and the tines of ring 320 held between sleeves 332 and 333 and the end portion 335 of sleeve 334 (as shown in FIG. 49). Then, anvil 70 is inserted into the incision 341. Sleeve 333 of tool 330 differs from sleeve 74 of tool 79 in that sleeve 333 has two concentric slots 333A and 333B, each of which is circular or oblong, for receiving a tubular central portion (of a tined anastomosis ring) having a different diameter. Thus, an anastomosis ring having a smaller diameter tubular central portion (a tubular central portion having smaller diameter than that of tubular portion 321) can be loaded onto tool 330 with its smaller diameter tubular central portion in slot 333A.

After ring 320 has been loaded and anvil 70 has been inserted into incision 341, sleeves 331, 332, 333, and 334 are advanced distally together as a unit to drive the tines of ring 320 between anvil 70 and the incised tissue edges, until the tines' tips engage the tine-forming surface 70A of anvil 70 and begin to curl radially outward (away from the central axis of anvil 70) as they advance against anvil surface 70A. Sleeves 331, 332, 333, and 334 continue to advance until they reach the position shown in FIG. 50, in which they have pressed part of the horizontal portion 322 of each tine against the exterior surface of vessel 340 and caused the distal portion 323 of each tine to curl (against stationary surface 70A of anvil 70) relative to the rest of ring 220 until the tip of each tine has penetrated (and grabbed) the tissue around the incision 341.

Then, as shown in FIG. 51, sleeve 331 is retracted in the proximal direction (toward the top of FIG. 51) while sleeves 332, 333, and 334 and anvil remain stationary in engagement with ring 320.

Then, anvil 70 is retracted (in the proximal direction) relative to sleeves 332, 333, and 334 into the position shown in FIG. 52. In response to the force exerted by anvil 70 on ring 320's tines (and the edges of tissue 340 that have been grabbed by the tines), each tine folds or buckles at both its weak portion (at location 327 shown in FIG. 52) and at the location along its length (identified by reference numeral 326 in FIG. 52) adjacent to the radially inner edge of sleeve 332's distal end portion, so that the curled distal portion 323 moves radially outward (away from anvil 70's central longitudinal axis) while it continues to grab the tissue, thereby everting the tissue edges. The radially inner surface of sleeve 332 has a recessed portion 332A to provide clearance for distal portion 323 as distal portion 323 moves radially outward. Each tine preferably has a weak portion (e.g., a hinge) at a location spaced from location 326. In one implementation, this weak portion is determined by a hole in each tine. Each hole is preferably located along the tine such that, when the tines are in their final configuration (shown in FIG. 57), the portion of each tine that is farthest (radially)

from the ring's tubular portion 321 coincides with (or is very near to) the hole; not with location 326.

Each tine preferentially bends at both location 326 and at its weak portion 327 during the steps described with reference to FIGS. 52 and 54–57.

After the folding or buckling of the tines described with reference to FIG. 52, sleeve 332 is retracted in the proximal direction (into the position shown in FIG. 53), leaving ring 320 held between sleeves 333 and 334.

Then, sleeve 331 and anvil 70 are advanced distally relative to sleeve 332 until curved distal end surface 331A of sleeve 331 engages the tines of ring 320 (as shown in FIG. 54). Sleeve 331 then continues to advance so that the tines ride along surface 331A so as to rotate the curled distal portion 323 of each tine radially outward into the configuration shown in FIG. 54. This moves the everted tissue adjacent to the tines radially outward, and further everts the everted tissue.

Then, sleeve 332 is advanced distally relative to sleeves 331 and 333 (and anvil 70) until sleeve 332's distal end engages the curled distal portion 323 of each tine. Sleeve 332 then continues to advance so as to rotate each curled distal portion 323 further radially outward into the configuration shown in FIG. 55, while surface 331A engages the intima of the everted tissue (to prevent radially inward movement of the everted tissue). This further everts the everted tissue and allows sleeve 332 to more easily form a final bend in each tine (in the step to be described with reference to FIG. 57).

Then, anvil 70 and sleeve 331 are retracted in the proximal direction into the position shown in FIG. 56, without exerting force on ring 320 or the everted tissue.

Then, sleeve 332 is advanced in the distal direction (relative to sleeves 333 and 334) to bend and rotate each tine (relative the rest of ring 320) from the configuration shown in FIG. 56 to that shown in FIG. 57, by pressing curled distal portion 323 of each tine (and the tissue adjacent thereto) against portion 335 of sleeve 334. This final bending and rotation further everts the tissue edges around incision 341. With ring 320 so installed in the incision 341 in its final configuration, its tines hold the incised tissue edges in the desired everted state (so that the everted tissue can be joined to tissue of another vessel or other organ).

After installation of ring 320, sleeve 334 is (e.g., portions comprising the distal end of sleeve 334 are) spread or dilated (radially outward away from anvil 70's central axis of symmetry) to decouple tool 330 from the installed ring, and tool 330 is removed from the installed ring.

Tool 330 is simpler than above-described tool 230 in that it has only four advanceable and retractable sleeves (331, 332, 333, and 334), whereas tool 230 has five such sleeves (sleeves 231, 232, 233, 234, and 235).

A preferred embodiment of the invention will be described with reference to FIGS. 58, 59, 60, and 61. Anastomosis ring 380 of FIGS. 58–61 is installed around an incision in the side wall of blood vessel 378, with curled tines 381 of ring 380 holding the incised tissue edges of vessel 380 with their intima 378A exposed for anastomosis with vessel 379. Four docking tabs (or "fingers") 383 extend out from ring 380's tubular central portion (parallel to the central longitudinal axis of ring 380, which is generally vertical in FIG. 58). There is a hole 384 at the base of each tab 383, defining a weak portion at which tab 383 will preferentially bend in response to exertion of radially outward bending force on its distal end 383A.

FIG. 61 shows ring 380 in its pre-installation configuration. Note that each tine 381 of ring 380 in the pre-installation configuration has a proximal portion which extends radially inward (perpendicular to ring 380's central axis of symmetry) toward the center of ring 380's tubular portion, and a distal (tip) portion extending perpendicular to such proximal portion. The "flat" tine geometry of ring 380 of FIG. 61 (the term "flat" denotes that the proximal portions of tines 381 are all coplanar, in a plane perpendicular to the ring's central axis of symmetry) is preferred over the "angled" tine geometry of ring 60 of FIG. 10 (in which the tines have proximal portions which extend at a 45 degree angle relative to the ring's central axis of symmetry, e.g., ring 60's central axis of symmetry).

Anastomosis ring 400 is installed around an incision in the side wall of blood vessel 379, with curled tines 401 of ring 400 holding the incised tissue edges of vessel 379 with their intima (not visible in FIG. 58) exposed for anastomosis with vessel 378. In order to align the tubular central portion of ring 380 with the tubular central portion of ring 400, vessel 379 is gripped by flat end forceps (or "graspers") 420, and moved toward tabs 383 of ring 380 so that tabs 383 enter the space 403 between the everted tissue of vessel 379 and the tubular central portion of ring 400.

FIG. 59 shows ring 400 being aligned with ring 380, with tabs 383 of ring 380 extending upward through ring 400's tubular central portion. Forceps 420 are lowering vessel 379 and ring 400 along tabs 383 toward the tubular central portion of ring 380, which in turn rests on vessel 378 and the tissue 377 which surrounds vessel 378. In FIG. 59, two arms of forceps 420 are squeezing together opposite side walls of vessel 379. As apparent from FIG. 59, the tubular central portion of ring 400 has greater diameter than that of ring 380, so that the two rings can be aligned together with their tubular central portions aligned vertically (as shown in FIG. 60, in which the tubular central portion of ring 380 is not visible since it is within that of ring 400).

After rings 380 and 400 have been aligned as shown in FIG. 60, forceps 420 release vessel 379. Two arms of forceps 420 (which can be the same arms as were used to align the rings, but which preferably are another pair of arms of an implementation of forceps 420 having two pairs of arms) are then moved into engagement with the tabs 383 (e.g., slightly separated arms of forceps 420 are moved into engagement with one pair of opposed tabs 383, and then the other pair of opposed tabs 383). The tab-manipulating arms of forceps 420 are moved downward (when viewed as in FIG. 60) to exert bending force on tabs 383 to bend them radially outward into the locking configuration shown in FIG. 60. In the locking configuration, tabs 383 extend generally horizontally outward, away from the common central axis of symmetry of rings 380 and 400, to lock rings 380 and 400 firmly together against tissue 377 with the exposed intima of vessel 378 sealed against the exposed intima of vessel 379.

It is understood that while certain forms of the present invention have been illustrated and described herein, the invention is not to be limited to the specific forms or arrangements of parts described and shown or the specific methods described.

What is claimed is:

1. A ring for use in preparing a first organ having an orifice for anastomosis with a second organ, said ring comprising:
   a ring portion sized to extend around the orifice of the first organ; and malleable tines extending radially inward from the ring portion, and having free distal ends deformed by a bending force into a configuration such that tips of said free distal ends curl toward portions of said tines from which said distal tips extend, each of said tines further having a weak portion between said ring portion and said free distal end, each of said tines further bent in a location of said weak portion, in a direction opposite to a direction of bending of said tips.

2. The ring of claim 1, wherein said each of the tines has two opposed major faces and a flat cross-section.

3. The ring of claim 2, wherein the weak portion is a section of said each of the tines through which at least one hole extends from one of the faces to another of said faces.

4. The ring of claim 1, wherein the ring portion is a tubular ring portion having a top edge and a bottom edge, and said ring also includes:

at least one fastener element extending out from the ring portion.

5. The ring of claim 4, wherein the fastener element is a malleable tab that extends upward from the top edge of the tubular ring portion.

6. The ring of claim 5, wherein the tab has a weak portion at the top edge of the tubular ring portion.

7. The ring of claim 6, wherein the weak portion of the tab is a notched section of the tab.

8. The ring of claim 4, wherein the fastener element is a tab which extends out from one of the top edge and the bottom edge of the ring portion and has a free distal end portion which extends radially outside of the ring portion.

9. The ring of claim 1, wherein said weak portions have a predefined configuration to cause said tines to preferentially deform in locations of said weak portions when said bending force is applied.

10. The ring of claim 1, wherein said tines substantially maintain said final, deformed configuration after removal of said bending force therefrom.

11. A ring for use in preparing a first organ having an orifice for anastomosis with a second organ, said ring comprising:

a ring portion sized to extend around the orifice; and malleable tines extending radially inward from the ring portion, each of said tines, when in a final configuration, having a proximal portion which extends radially inward away from the ring portion, a distal portion folded toward a portion of said tine from which said distal portion extends, for holding tissue of the first organ in an everted state, and a central portion between the proximal portion and the distal portion, and said each of the tines in the final configuration is bent radially outward at said central portion toward the ring portion.

12. The ring of claim 11, wherein the ring portion is a tubular ring portion having a top edge and a bottom edge.

13. The ring of claim 12, also including:

at least one fastener element extending out from the ring portion.

14. The ring of claim 13, wherein the fastener element is a malleable tab element which extends generally vertically from one of the top edge and the bottom edge of the ring portion.

15. The ring of claim 13, wherein the fastener element is a tab which extends out from one of the top edge and the bottom edge of the ring portion and has a free distal end portion which extends radially outside of the ring portion.

16. The ring of claim 11, wherein the distal portion of said each of the tines in the final configuration is shaped for piercing said tissue of the first organ.

* * * * *